US008486719B2

(12) United States Patent
Roby et al.

(10) Patent No.: US 8,486,719 B2
(45) Date of Patent: Jul. 16, 2013

(54) MULTIPLEX ASSAY METHODS AND COMPOSITIONS

(75) Inventors: Philippe Roby, Montreal (CA); Roger Bosse, Longueuil (CA); Mathieu Arcand, Montreal (CA)

(73) Assignee: PerkinElmer BioSignal, Inc., Montreal, Quebec (CA)

( * ) Notice: Subject to any disclaimer, the term of this patent is extended or adjusted under 35 U.S.C. 154(b) by 455 days.

(21) Appl. No.: 12/710,136

(22) Filed: Feb. 22, 2010

(65) Prior Publication Data

US 2010/0304403 A1  Dec. 2, 2010

Related U.S. Application Data

(60) Provisional application No. 61/154,008, filed on Feb. 20, 2009, provisional application No. 61/154,011, filed on Feb. 20, 2009, provisional application No. 61/251,849, filed on Oct. 15, 2009.

(51) Int. Cl.
*G01N 33/543* (2006.01)

(52) U.S. Cl.
CPC .................................. *G01N 33/543* (2013.01)
USPC ........... 436/518; 435/7.9; 435/7.92; 436/501; 436/523; 436/524

(58) Field of Classification Search
None
See application file for complete search history.

(56) References Cited

U.S. PATENT DOCUMENTS

| | | | |
|---|---|---|---|
| 5,340,716 A | 8/1994 | Ullman et al. | |
| 5,656,207 A | 8/1997 | Woodhead et al. | |
| 6,153,442 A | 11/2000 | Pirio et al. | |
| 6,406,667 B1 | 6/2002 | Singh et al. | |
| 6,797,481 B1 | 9/2004 | Ullman et al. | |
| 7,033,775 B2 | 4/2006 | Ullman et al. | |
| 7,101,682 B2 | 9/2006 | Ullman et al. | |
| 7,217,531 B2 | 5/2007 | Singh et al. | |
| 7,279,286 B2 | 10/2007 | Kannt et al. | |
| 7,371,745 B2 | 5/2008 | Ebright et al. | |
| 2004/0175696 A1 | 9/2004 | Ullman et al. | |
| 2007/0077588 A1 | 4/2007 | Will | |
| 2008/0261239 A1 | 10/2008 | Roby et al. | |

FOREIGN PATENT DOCUMENTS

| | | |
|---|---|---|
| EP | 0484027 | 5/1992 |
| WO | WO-01/84157 | 11/2001 |
| WO | WO-2004011900 | 2/2004 |
| WO | WO-2007/096459 | 8/2007 |
| WO | WO-2008/104637 | 9/2008 |

OTHER PUBLICATIONS

Taouji et al., Current Screens Based on the alpaScreen technology for Deciphering Cell Signalling Pathways, current Genomics, Apr. 2009, 10, pp. 93-101.*

Krica., Clinical applications of chemiluminescence, Analytica Chimica Acta 500, (2003), pp. 279-286.*

Arcand, M. et al. "Single-well simultaneous measurement of MAP2K MEK1 activity and interaction with the MAP kinase ERK2 using AlphaScreen and AlphaLISA platforms," poster presented as part of the Society for Biomolecular Sciences 15th Annual Conference and Exhibition, Lille, France, Apr. 26-30, 2009.

Guenat, S. et al., Homogeneous and Nonradioactive High-Throughput Screening Platform for the Characterization of Kinase Inhibitors in Cell Lysates, *Journal of Biomolecular Screening*, 11(8): 1015-1026, 2006.

Rininsland, F. et al., Metal ion-mediated polymer superquenching for highly sensitive detection of kinase and phosphatase activities, *PNAS*, 101(43): 15295-15300, 2004.

Ullman, et al., Luminescent oxygen channeling immunoassay: Measurement of particle binding kinetics by chemiluminescence, *Proc. Natl. Acad. Sci. USA*, 91, 5426-5430, Jun. 1994.

Arcand, M. et al., Single-Well Monitoring of Protein-Protein Interaction and Phosphorylation-Dephosphorylation Events, *Biochemistry*, 49: 3213-15, 2010.

Beaudet, L. et al., AlphaLISA™ immunoassays: the no-wash alternative to ELISAs for research and drug discovery, *Nature Methods*, 5: 8-9, Dec. 2008.

Dahan, S. et al., Antibody-based Proteomics: From bench to bedside, Proteomics Clinical Applications, 1: 922-33, 2007.

Eglen et al., The Use of AlphaScreen Technology in HTS: Current Status, Current Chemical Genomics, 1: 2-10, 2008.

Meza, M., Bead-based HTS applications in drug discovery, Drug Discovery Today, 1(1): 38-41, Jun. 2000.

Rouleau, N. et al, Development of a Versatile Platform for Nuclear Receptor Screening Using AlphaScreen☐, Journal of Biomolecular Screenning , 8: 191-97, 2003.

Ullman, et al., Luminescent oxygen channeling immunoassay: Measurement of particle binding kinetics by chemiluminescence, *Proc. Natl. Acad. Sci. USA*, 91, 5426-5430, 1994.

\* cited by examiner

*Primary Examiner* — Gary W Counts
(74) *Attorney, Agent, or Firm* — Gifford, Krass, Sprinkle, Anderson & Citkowski, P.C.

(57) ABSTRACT

Luminescence assays and compositions for assay of biomolecular interaction and activity and detection of modulators of biomolecular interaction and activity are provided. Technology described herein has utility in a variety of assay formats and types, for example, simultaneous monitoring multiple parameters which affect interaction and activity of biological molecules. Compositions and methods are provided herein which include a first solid-phase support associated with a first specific binding agent and a photosensitizer; a second solid-phase support associated with a second specific binding agent and a first emission system; and a third solid-phase support associated with a third specific binding agent and a second emission system.

21 Claims, 16 Drawing Sheets

MKP-2

MULTIPLEX ASSAY METHODS AND COMPOSITIONS

This application claims priority to U.S. Provisional Application Ser. Nos. 61/154,008 and 61/154,011, both filed Feb. 20, 2009, and 61/251,849, filed Oct. 15, 2009. The entire content of each application is incorporated herein by reference.

FIELD OF THE INVENTION

The present invention relates generally to methods and compositions for assay of interaction and activity of biological molecules as well as detection of modulators thereof. Specific aspects of the present invention relate to luminescence assays and compositions for assay of interaction and activity of biological molecules and detection of modulators thereof.

SUMMARY OF THE INVENTION

Assay methods are provided according to embodiments which include providing an assay mixture which includes a first solid-phase support associated with a first specific binding agent and a photosensitizer, the photosensitizer light excitable to activate oxygen to produce singlet oxygen. The assay mixture also includes a second solid-phase support associated with a second specific binding agent and a first emission system. The first emission system includes a first energy acceptor activated by singlet oxygen, the first emission system activated by singlet oxygen to emit a first light signal characterized by a first emission spectrum. The assay mixture further includes a third solid-phase support including a third specific binding agent and a second emission system comprising a second energy acceptor activated by singlet oxygen, the second emission system activated by singlet oxygen to emit a second light signal characterized by a second emission spectrum, wherein the first light signal and second light signal are distinguishable. The assay mixture is irradiated using a light source, thereby activating the photosensitizer to produce singlet oxygen. The first light signal and the second light signal are then detected. The first light signal is indicative of proximity of a first target bound to the first specific binding agent and a second target bound to the second specific binding agent. The second light signal is indicative of proximity of the first target bound to the first specific binding agent and third target bound to the third selective binding agent.

In particular embodiments, the first solid-phase support, second solid-phase support and third solid-phase support are particles.

In further embodiments, the first solid-phase support is a cell or cell membrane and the second solid-phase support and third solid-phase support are particles.

In a particular option, the first emission spectrum is characterized by an emission maximum in the range of 450-600 nm and the second emission spectrum is characterized by an emission maximum in the range of 590-670 nm.

In a further option, the first emission spectrum is characterized by an emission maximum in the range of 545-580 nm and the second emission spectrum is characterized by an emission maximum in the range of 600-620 nm.

An included photosensitizer is phthalocyanine according to embodiments of described assays and compositions.

The first energy acceptor and second energy acceptor activated by singlet oxygen is thioxene according to embodiments of described assays and compositions.

The first emission system includes an anthracene and rubrene according to embodiments of described assays and compositions. The second emission system includes a europium chelate according to embodiments of described assays and compositions.

According to embodiments of described assays and compositions, the first interacting member is an enzyme, the second interacting member is a substrate for the enzyme and the third specific binding agent selectively interacts with enzyme-modified substrate. For example, the enzyme is a kinase, the substrate is a substrate of the kinase and the third specific binding agent selectively binds to the substrate phosphorylated by the kinase. In a further example, the enzyme is a phosphorylase, the substrate is a phosphorylated protein or peptide and the third specific binding agent selectively binds to a phosphorylated protein or peptide or non-phosphorylated protein or peptide.

Optionally, a test compound is included in the assay mixture. An assay described herein further includes comparing the first light signal and the second light signal in the absence of the test compound with the first light signal and the second light signal in the presence of the test compound.

Compositions are provided herein which include a first solid-phase support associated with a first specific binding agent and a photosensitizer, the photosensitizer light excitable to activate oxygen to produce singlet oxygen; a second solid-phase support associated with a second specific binding agent and a first emission system including an energy acceptor activated by singlet oxygen, the first emission system activated by singlet oxygen to emit a first light signal characterized by a first emission spectrum; and a third solid-phase support associated with a third specific binding agent and a second emission system comprising an energy acceptor activated by singlet oxygen, the second emission system activated by singlet oxygen to emit a second light signal characterized by a second emission spectrum, wherein the first light signal and second light signal are distinguishable.

Assay methods are provided which include providing an assay mixture including a first solid-phase support associated with a photosensitizer, the photosensitizer light excitable to activate oxygen to produce singlet oxygen. The first solid-phase support further includes a first member of a selective binding pair selected from the group consisting of: enzyme/ known or putative enzyme substrate; receptor/known or putative ligand; antibody/antigen; and nucleic acid/complementary nucleic acid. The assay mixture further includes a second solid-phase support associated with a second specific binding agent and a first emission system comprising a first energy acceptor activated by singlet oxygen, the first emission system activated by singlet oxygen to emit a first light signal characterized by a first emission spectrum. The second solid-phase support is associated with a second member of the selective binding pair selected from the group consisting of: enzyme/enzyme substrate; receptor/ligand; antibody/antigen; and nucleic acid/complementary nucleic acid. The assay mixture further includes a third solid-phase support associated with a third specific binding agent and a second emission system comprising a second energy acceptor activated by singlet oxygen, the second emission system activated by singlet oxygen to emit a second light signal characterized by a second emission spectrum, wherein the first light signal and second light signal are distinguishable, wherein the third specific binding agent selectively binds to a modification of the first or second member of the selective binding pair. Methods provided further include irradiating the assay mixture with a light source, thereby activating the photosensitizer to produce singlet oxygen. The first light signal and the second light signal are then detected, wherein detecting the first light signal is indicative of binding of the first member of the selective binding pair with the second member of the selective binding pair and wherein detecting the second light signal is indicative of selective binding of the specific binding agent to a modification of the first or second member of the selective binding pair. Optionally, a test compound is included in the assay mixture. An assay described herein further includes comparing the first light signal and the second light signal in the absence of the test compound with the first light signal and the second light signal in the presence of the test compound.

Assays are provided which include providing an assay mixture including a cell having a cell membrane, the cell comprising a first specific binding agent and a photosensitizer associated with the cell membrane, the photosensitizer light excitable to activate oxygen to produce singlet oxygen. The assay mixture includes a first solid-phase support associated with a second specific binding agent and a first emission system including a first energy acceptor activated by singlet oxygen, the first emission system activated by singlet oxygen to emit a first light signal characterized by a first emission spectrum. The assay mixture is irradiated with a light source, thereby activating the photosensitizer to produce singlet oxygen. The first light signal is then detected, wherein detecting the first light signal is indicative of proximity of a first target bound to the first specific binding agent and a second target bound to the second specific binding agent.

The assay mixture optionally includes a second solid-phase support associated with a third specific binding agent and a second emission system including a second energy acceptor activated by singlet oxygen, the second emission system activated by singlet oxygen to emit a second light signal characterized by a second emission spectrum, wherein the first light signal and second light signal are distinguishable, and wherein detecting the second light signal is indicative of proximity of the first target bound to the first specific binding agent and third target bound to the third selective binding agent.

In some embodiments, the first solid-phase support is a particle. In further embodiments, the second solid-phase support is a particle.

Each of the first, second and third specific binding agents can be, without limitation, a receptor, a ligand, an antibody, an antigen, a lipid, a carbohydrate, a peptide, an oligosaccharide and a lectin.

DETAILED DESCRIPTION OF THE PREFERRED EMBODIMENTS

Figure 1:
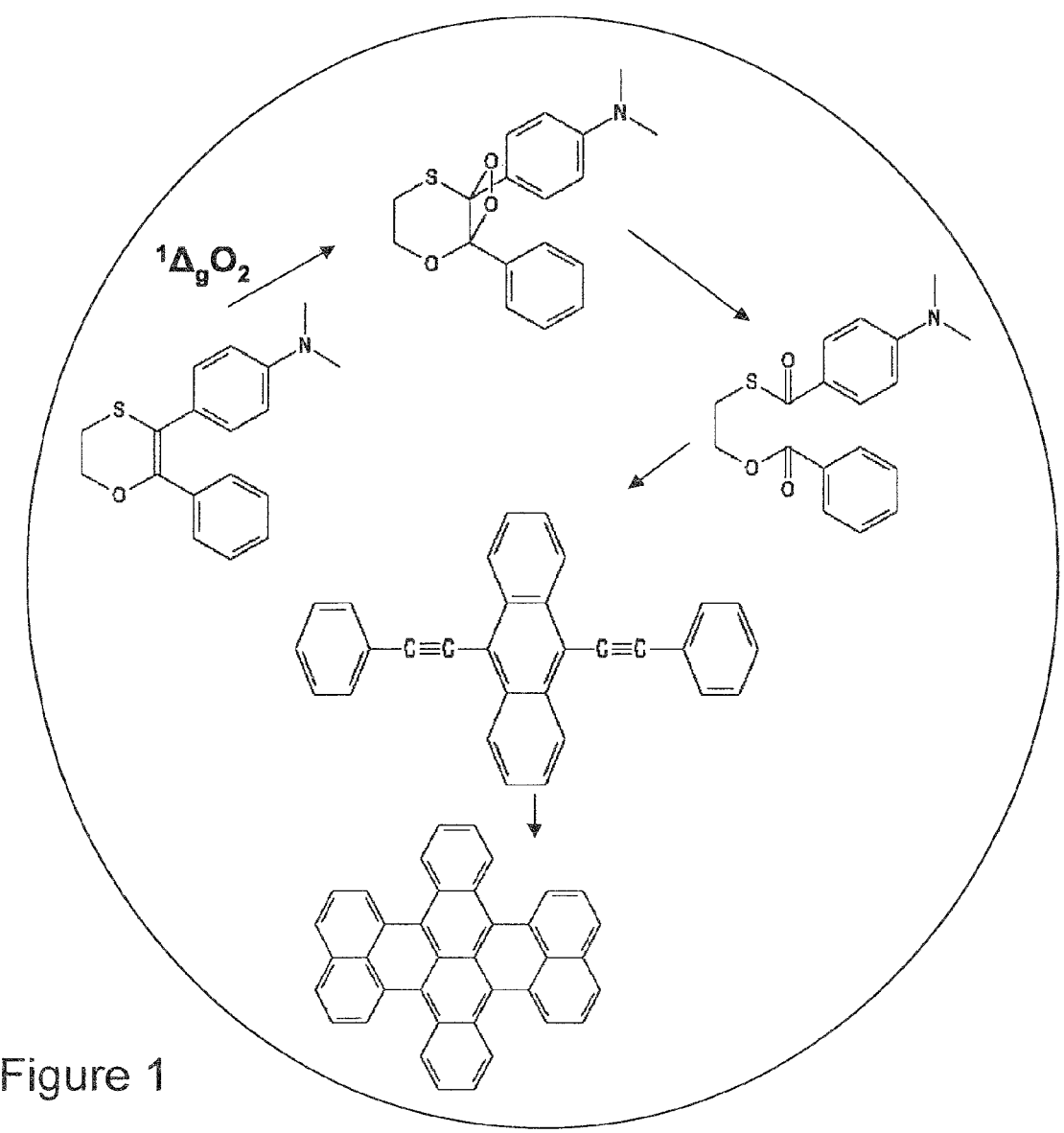
FIG. 1 is an image schematically showing an acceptor bead and an included emission system.

Luminescence assays and compositions for assay of biomolecular interaction and activity and detection of modulators of biomolecular interaction and activity are provided.

The technology described herein has utility in a variety of assay formats and types, for example, simultaneous monitoring at least two parameters which affect interaction and activity of biological molecules. For example, assay methods and compositions described herein have utility in pharmacological characterization of test compounds acting on enzymes such as ATP reversible and irreversible blockers; inhibitors; allosteric modulators and orthosteric modulators.

Methods and compositions described herein have utility in numerous assays types and allow for detection and monitoring of presence and levels of multiple analytes in a sample, detection and monitoring of analyte association order, mutually exclusive binding relationships, scaffolding proteins and multimeric complexes. Assays and compositions of the present invention are provided for screening of test compounds to determine their target in an enzyme cascade. Assays and compositions of the present invention are provided for detection and monitoring of expression and changes in expression of various analytes. Assays and compositions of the present invention are provided for detection and monitoring of enzyme activity and post-translational modification of enzyme substrates.

Assay methods according to embodiments of the present invention include providing an assay mixture. The assay mixture includes a first solid-phase support associated with a first specific binding agent and a photosensitizer, a second solid-phase support associated with a second specific binding agent and a first emission system, and a third solid-phase support associated with a third specific binding agent and a second emission system.

The assay mixture is irradiated with a light source, and light signals are generated which are indicative of 1) proximity of the first solid-phase support and the second solid-phase support and 2) proximity of the first solid-phase support and the third solid-phase support. The proximity of the solid-phase supports is indicative of biomolecular interaction and/or activity of specific binding agents associated with the supports and included in the assay mixture.

The term "specific binding agent" refers to one member of a complex, such as a member of a binding pair, capable of forming a stable covalent or non-covalent association with a second member of the complex. Examples of specific binding agents include, without limitation, analytes, ligands, receptors, antibodies, antigens, lipids, carbohydrates, peptides, oligosaccharides, lectins, nucleic acids, aptamers, epitope tags such as a polyhistidine tag, a metal bound by a polyhistidine tag, biotin, avidin, streptavidin, and digoxigenin. Examples of binding pairs include, without limitation, enzyme/enzyme substrate; receptor/ligand, antibody/antigen; polyhistidine tag/metal; nucleic acid/substantially complementary nucleic acid, nucleic acid/complementary nucleic acid, and avidin or streptavidin/biotin. Specific binding of a specific binding agent with another specific binding agent can be characterized by a dissociation constant indicative of affinity between the two specific binding agents. Dissociation constants indicative of specific binding between specific binding agents are generally in the range of about $10^{-4}$ M to about $10^{-12}$ or less, and preferably in the range of about $10^{-8}$ M to about $10^{-12}$ M or less. Specific binding agents can be naturally derived or can be partially or wholly synthetic.

The term "solid-phase support" refers to a porous or non-porous member which is substantially non-soluble in an aqueous medium included in an assay mixture. A solid-phase support can be solid, semi-solid, gel or a mixture thereof and can have a form illustratively including, but not limited to, a microtiter plate; a chip; a particle, such as a bead; a fiber, a mesh, a pin, a membrane, such as a nitrocellulose membrane; a container; and a cell or cell membrane. A solid-phase support includes, without limitation, glass; metal; ceramic; plastic, such as polycarbonate, polypropylene, polystyrene, nylon; paper; silicon; cellulose, nitrocellulose, agarose, dextran, polyacrylamide; or any other material to which a specific binding agent can be associated for use in an assay of the present invention.

The term "associated with" referring to a solid-phase support and a specific binding agent, photosenstizer, or component of an emission system, refers to covalent or non-covalent binding of the solid-phase support and the specific binding agent, photosenstizer, or component of an emission system. Methods for associating a specific binding agent, photosenstizer, or component of an emission system with a solid-phase support are well-known in the art. A solid-phase support can include functional groups for association of a specific binding agent. For example, a solid-phase support can include carboxyl, amine, amino, carboxylate, halide, ester, alcohol, carbamide, aldehyde, chloromethyl, sulfur oxide, nitrogen oxide, epoxy and/or tosyl functional groups. Functional groups of solid-phase supports, modification thereof and association of a specific binding agent thereto are described, for example, in Fitch, R. M., Polymer Colloids: A Comprehensive Introduction, Academic Press, 1997.

A linker or coating can be employed to associate a solid-phase support and a specific binding agent, photosenstizer, or component of an emission system, using methods well-known to the skilled artisan.

A specific binding agent, photosenstizer, or component of an emission system, can be modified, such as by inclusion of a functional group, to facilitate association with a solid-phase support.

Exemplary methods of associating a solid-phase support and a specific binding agent, photosenstizer, and/or component of an emission system are described in detail herein and in U.S. Pat. Nos. 5,340,716; 5,516,636; 5,536,834; 5,709,994; 5,763,602; 6,251,581; 6,406,667; 6,797,481; 7,033,775; 7,101,682; N. J. Turro, "Molecular Photochemistry", page 132, W. A. Benjamin Inc., New York 1965; Ullman, et al., Proc. Natl. Acad. Sci. USA 91, 5426-5430 (1994); Strong et al, Ann. New York Acad. Sci., 745: 297-320 (1994); Martin et al, Methods Enzymol., 186: 635-645 (1990); Yarmush et al, Crit. Rev. Therapeutic Drug Carrier Syst., 10: 197-252 (1993); Wohrle, Chimia, 45: 307-310 (1991); Thetford, European patent publ. 0484027; Sessler et al, SPIE, 1426: 318-329 (1991); Madison et al, Brain Research, 522: 90-98 (1990); Polo et al, Inorganica Chimica Acta, 192: 1-3 (1992); and Demas et al, J. Macromol. Sci., A25: 1189-1214 (1988).

In particular aspects, a solid-phase support is a particle, such as a bead. The particles can be of any shape, such as cylindrical, spherical, and so forth, size, composition, or physiochemical characteristics.

Microparticles, such as microbeads, used can have a diameter of less than one millimeter, for example, a size ranging from about 0.1 to about 1,000 micrometers in diameter, inclusive, such as about 3-25 microns in diameter, inclusive, or about 5-10 microns in diameter, inclusive. Nanoparticles, such as nanobeads used can have a diameter from about 1 nanometer (nm) to about 100,000 nm in diameter, inclusive, for example, a size ranging from about 10-1,000 nm, inclusive, or for example, a size ranging from 200-500 nm, inclusive. In certain embodiments, particles used are beads, particularly microbeads and nanobeads.

Particles are illustratively organic or inorganic particles, such as glass; metal; ceramic; plastic, such as polycarbonate, polypropylene, polystyrene, nylon; paper; silicon; cellulose, nitrocellulose, agarose, dextran, polyacrylamide; or any other material to which a specific binding agent can be associated for use in an assay of the present invention. Particles are latex beads in particular embodiments.

The term "photosensitizer" refers to a light excitable molecule which activates oxygen to produce singlet oxygen. Exemplary photosensitizers include, without limitation, acetone, benzophenone, chlorophylls, 9,10-dibromoanthracene, eosin, fullerenes, methylene blue, metalloporphyrins, such as hematoporphyrin, phthalocyanines, such as $Al^{3+}$ phthalocyanines, $Cu^{2+}$ phthalocyanines and $Zn^{2+}$ phthalocyanines, rose Bengal and 9-thioxanthone. These and other photosensitizers are described in U.S. Pat. Nos. 5,340,716; 5,516,636; 5,536,834; 5,709,994; 5,763,602; 6,251,581; 6,406,667; 6,797,481; 7,033,775; 7,101,682; N. J. Turro, "Molecular Photochemistry", page 132, W. A. Benjamin Inc., New York 1965; Ullman, et al., Proc. Natl. Acad. Sci. USA 91, 5426-5430 (1994); Strong et al, Ann. New York Acad. Sci., 745: 297-320 (1994); Martin et al, Methods Enzymol., 186: 635-645 (1990); Yarmush et al, Grit. Rev. Therapeutic Drug Carrier Syst., 10: 197-252 (1993); Wohrle, Chimia, 45: 307-310 (1991); Thetford, European patent publ. 0484027; Sessler et al, SPIE, 1426: 318-329 (1991); Madison et al, Brain Research, 522: 90-98 (1990); Polo et al, Inorganica Chimica Acta, 192: 1-3 (1992); and Demas et al, J. Macromol. Sci., A25: 1189-1214 (1988).

The term "emission system" refers to two or more substances associated with a solid-phase substrate, at least one of which reacts with singlet oxygen, selected to emit radiation having desired emission characteristics. An emission system having two components includes a first acceptor material excitable by singlet oxygen to transfer energy to a second acceptor material and a second acceptor material that accepts energy transferred from the first acceptor material and emits fluorescent light. Using an emission system that includes two substances, singlet oxygen produced by a photosensitizer diffuses to the solid phase substrate containing the emission system and reacts with a first acceptor material excitable by singlet oxygen. The first acceptor material then transfers energy to a second acceptor material which emits fluorescent light.

An emission system having more than two components includes at least a first acceptor material excitable by singlet oxygen to transfer energy to a second acceptor material, a second acceptor material that accepts energy transferred from the first acceptor material and transfers energy to a third acceptor material which emits fluorescent light. Using an emission system that includes more than two substances, singlet oxygen produced by the photosensitizer diffuses and reacts with a first material excitable by singlet oxygen to release energy. The first acceptor material transfers energy to a second acceptor material which emits fluorescent radiation or which transfers energy to a third acceptor material. The third acceptor material emits radiation or transfers energy to a fourth acceptor material which emits radiation. Additional acceptor materials can be included, for instance, to produce a desired wavelength of emitted radiation.

Materials excitable by singlet oxygen to release energy according to embodiments of the present invention are chemiluminescence reactant capable of reacting with singlet oxygen such that energy is transferred to an acceptor material in proximity to the chemiluminescence reactant. Exemplary chemiluminescence reactants include, but are not limited to, thioxenes, such as 1,4-thioxenes. Thioxene and related chemiluminescence reactants and methods of their preparation are described in Ullman et al., PNAS, USA, 91:5426-5439, 1994. Additional examples of such chemiluminescence reactants are described in U.S. Pat. Nos. 5,340,716; 5,516, 636; 5,536,834; 5,709,994; 5,763,602; 6,251,581; 6,406,667; 6,797,481; 7,033,775; and 7,101,682.

Acceptor materials are fluorescent dyes that emit fluoresce in a wavelength range from about 200 nm to about 1000 nm. Non-limiting examples of such fluorescent dyes generally include polycyclic aromatic hydrocarbon fluorescent dyes such as anthracene dyes illustratively including 9,10-bis(phenylethynyl)anthracene (BPEA), 9,10-diphenylanthracene (DPA) and derivatives thereof such as halogen and/or alkyl substituted anthracenes illustratively including 1-chloro-9, 10-bis(phenylethynyl)anthracene, 2-chloro-9,10-bis(phenylethynyl)anthracene, 2-ethyl-9,10-bis(phen ylethynyl)anthracene and 1,2-dimethyl-9,10-bis(phenylethyl)anthracene; napthacene dyes illustratively including tetraphenylnapthacene (rubrene) and 5,12-bis(phenylethynyl)napthacene, coumarins, oxazine dyes; phthalocyanines, porphyrins; polyacetylenes, squaraines, and such dyes as 4-acetamido-4'-isothiocyanatostilbene-2,2'-disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarins and derivatives such as coumarin, 7-amino-4-methylcoumarin (AMC, Coumarin 120), 7-amino-4-trifluoromethylcouluarin (Coumaran 151); cyanosine; DAPDXYL sulfonyl chloride; 4',6-diaminidino-2-phenylindole (DAPI); 5',5"-dibromopyrogallol-sulfonephthalein (Bromopyrogallol Red); 7-diethylamine-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl) amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), 5-(4,6-dichlorotriazin-2-yl) aminofluorescein (DTAF), 2', 7'-dimethoxy-4', 5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl}amino)naphthalene-1-sulfonic acid), Malachite Green isothiocyanate; 4-methyl umbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron .RTM. Brilliant Red 3B-A); rhodamine and derivatives such as 6-carboxy-X-rhodamine(ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N',N-tetramethyl-carboxyrhodamine (TAMRA); tetramethyl rhodamine; tetramethyl rhodamine isothiocyanate (TRITC); riboflavin; rosolic acid; bis-(4-dimethlyaminophenyl)squaraine; lanthanide chelates and cryptates such as, but not limited to, chelates and cryptates of dysprosium, erbium, europium, praseodymium, samarium, terbium, thulium, and ytterbium; chrysene; coronene; naphthalene; phenanthrene; pyrene; and perylene. Additional acceptor materials are described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005.

Figure 2:
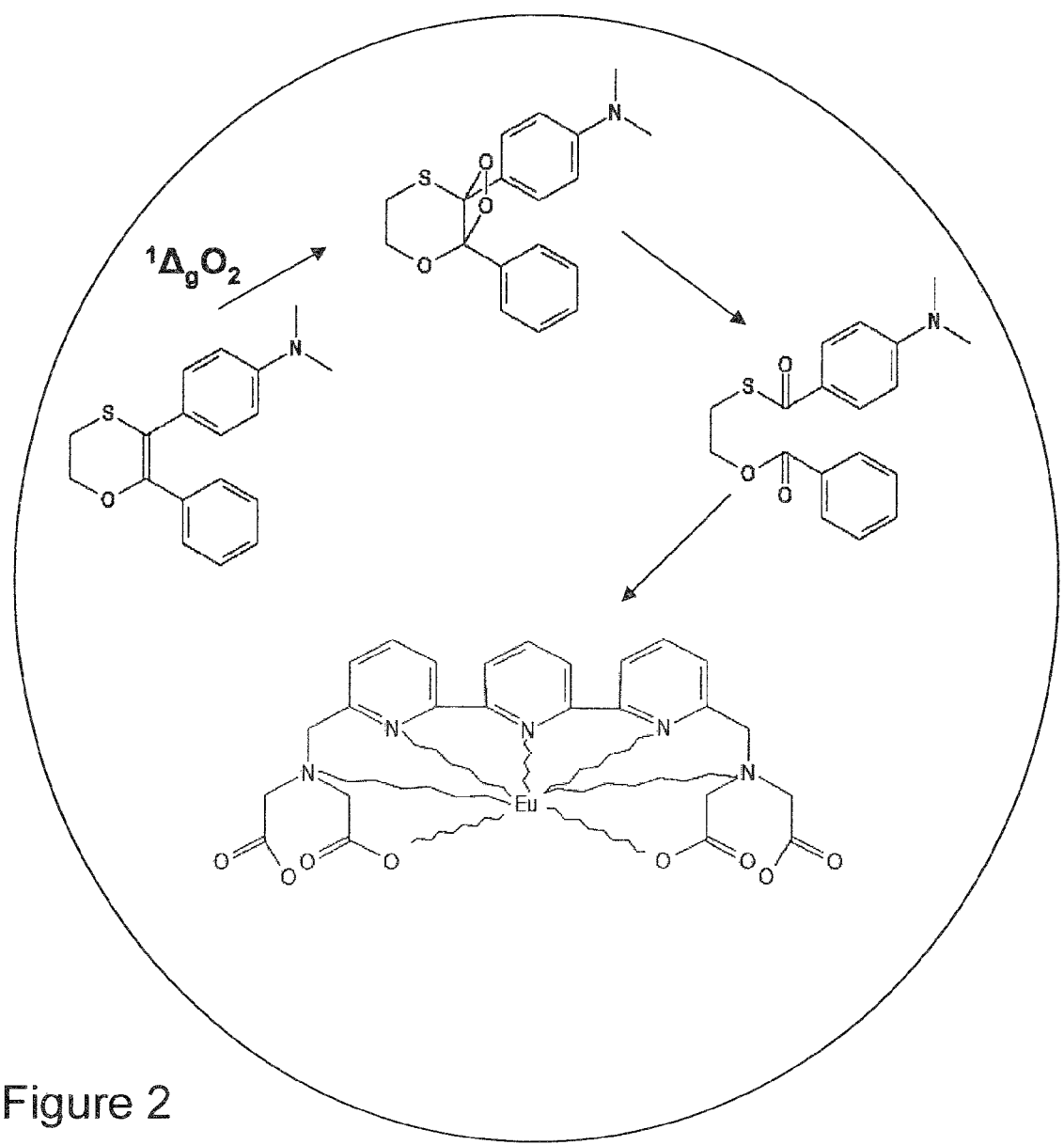
FIG. 2 is an image schematically showing an acceptor bead and an included emission system.

FIGS. 1 and 2 schematically illustrate solid-phase supports in the form of acceptor beads along with an included emission system. FIG. 1 illustrates an emission system including thioxene, 9,10-bis(phenylethynyl)anthracene and rubrene. FIG. 2 illustrates an emission system including thioxene and a europium chelate.

Assays according to the present invention are generally carried out under conditions suitable for biomolecular interaction and activity. The assay mixture generally includes an aqueous medium. The pH of the assay mixture is usually in the range of about pH 4-pH 11, preferably in the range of about pH 5-pH 10, and more preferably in the range of about pH 6-pH 8. One or more buffers can be included in the assay mixture illustratively including, but not limited to, borate, cacodylate, carbonate, citrate, HEPES, MES, MOPS, phosphate, PIPES, TAPS, TES and Tris buffers.

Temperatures employed in assays of the present invention are generally in the range of about 4° C.-45° C.

Where nucleic acids are included in an inventive assay, higher temperatures may be suitable to achieve specific hybridization.

Embodiments are provided in which the first solid-phase support, second solid-phase support and third solid-phase support are particles.

In further embodiments, the first solid-phase support is a cell membrane and the second solid-phase support and third solid-phase support are particles.

Embodiments of methods and compositions of the present invention include a first emission spectrum characterized by an emission maximum in the range of 450-600 nm and a second emission spectrum is characterized by an emission maximum in the range of 590-670 nm.

In further embodiments, the first emission spectrum is characterized by an emission maximum in the range of 545-580 nm and the second emission spectrum is characterized by an emission maximum in the range of 600-620 nm.

In particular embodiments, first specific binding agent is an enzyme which binds to the second specific binding agent, a substrate for the enzyme. The third specific binding agent specifically interacts with enzyme-modified substrate. In a non-limiting example, the enzyme is a kinase, the substrate is a substrate of the kinase and the third specific binding agent specifically binds to the substrate when it is phosphorylated at a phosphorylation site of the kinase.

In embodiments of the present invention, the first specific binding agent is specific for a modifiable target and the second and third specific binding agents are specific for modifications of the modifiable target. In a non-limiting example, the modifiable target is a kinase substrate and the second and third specific binding agents specifically bind to phosphorylation sites of the substrate when phosphorylated.

The term "enzyme" refers to a biological molecule that catalyzes biological reactions. In general, enzymes are proteins, illustratively including but not limited to, kinases, phosphatases, ubiquitin-conjugating enzymes, ubiquitin-activating enzymes and ubiquitin-ligating enzymes, ubiquitinases, methylases, demethylases, acetylases, deacetylases, sumoylation enzymes, polymerases, transferases, hydrolases, isomerases, ligases, oxidoreductases, ATPases, GTPasees and proteases. Certain enzymes are nucleic acids, such as catalytically active RNA molecules. The terms "enzyme substrate" and "substrate for an enzyme" refer to a naturally occurring or synthetic molecule upon which an enzyme acts to produce an enzyme-modified molecule. Enzyme substrates are generally proteins or peptides and can also be nucleic acids, lipids, carbohydrates and combinations thereof.

Methods of the present invention can be used to detect an effect of one or more test compounds on biomolecular interactions and/or activites assayed according to embodiments of the present invention. A test compound may be added to the assay mixture. Comparison of light signals generated in the presence and absence of the test compound may be performed.

A test compound used in a method of the present invention can be any chemical entity, illustratively including a synthetic or naturally occurring compound or a combination of a synthetic or naturally occurring compound, a small organic or inorganic molecule, a protein, a peptide, a nucleic acid, a carbohydrate, an oligosaccharide, a lipid or a combination of any of these. A library of test compounds can be used such as a spatially addressable solid phase libraries and solution phase libraries. A library of test compounds, suitable for use in high-thoughput methods of screening can be used. A library of test compounds is illustratively a library of compounds generated by combinatorial chemistry such as a library of small molecules, peptides, proteins, lipids, nucleic acids and phage display libraries.

Compositions are provided according to embodiments of the present invention which include a first solid-phase support comprising a first specific binding agent and a photosensitizer, the photosensitizer light excitable to activate oxygen to produce singlet oxygen; a second solid-phase support comprising a second specific binding agent and a first emission system comprising an energy acceptor activated by singlet oxygen, the first emission system activated by singlet oxygen to emit a first light signal characterized by a first emission spectrum; and a third solid-phase support comprising a third specific binding agent and a second emission system comprising an energy acceptor activated by singlet oxygen, the second emission system activated by singlet oxygen to emit a second light signal characterized by a second emission spectrum, wherein the first light signal and second light signal are distinguishable.

Embodiments of inventive compositions and methods are illustrated in the following examples. These examples are provided for illustrative purposes and are not considered limitations on the scope of inventive compositions and methods.

EXAMPLES

Example 1

Multiplexed detection using two types of acceptor beads and one type of donor bead are described in this example.

Donor beads contain the photosensitizer, phthalocyanine, which converts ambient oxygen to singlet oxygen upon light excitation at 680 nm. Donor beads also contain streptavidin as the specific binding agent.

Acceptor bead type 1 contains 3 acceptors: thioxene, 9,10-bis(phenylethynyl)anthracene and rubrene. The chemiluminescent reactant thioxene reacts with singlet oxygen to form an unstable 1,2-dioxetane intermediate which is readily converted to a more stable di-ester form. This conversion is followed by light production at 340-350 nm. Both 9,10-bis(phenylethynyl)anthracene and rubrene are fluors used to red-shift the emission of the chemiluminescent reaction through two consecutive fluorescence resonance energy transfer steps. Final emission of the type 1 acceptor beads is essentially due to rubrene fluorescence and is detected in the range of about 520-620 nm with a maximum emission of about 545-565 nm. Type 2 acceptor beads contain 2 acceptors: thioxene and a europium chelate. Similar to the type 1 acceptor beads, thioxene reacts with singlet oxygen to produce light at 340-350 nm which directly excites the europium chelate which then fluoresces in the range of about 610-620 with an emission maximum of about 613-617 nm.

Both type 1 and type 2 acceptor beads also contain biotin.

Streptavidin coated donor beads (10 ug/ml) are mixed with biotinylated acceptor beads (10 ug/ml) type 1 and type 2. The mixtures are incubated, irradiated with 680 nm light and fluorescent signals detected using an Envision 2101 reader equipped with an appropriate filter such as a Texas Red (555 nm), a dysprosium (572 nm) or an europium (615 nm) narrow band pass filters.

Distinct signals are detected from both types of acceptor beads interacting simultaneously with the donor beads, could be selectively discriminated using appropriate narrow band pass filters.

Example 2

Multiplexed assays were performed to detect two different analytes in solution: rat and rabbit IgGs, respectively. Biotinylated rabbit and rat IgG's were added, alone or in combination, to anti-rabbit IgG coated type 1 acceptor beads (10 ug/ml), Anti-rat IgG coated type 2 acceptor beads (10 ug/ml) and streptavidin donor beads (10 ug/ml). Increasing concentrations of biotinylated rat IgG's alone produced a robust signal increase only detectable in the 615 nm channel. Increasing concentrations biotinylated rabbit IgG's alone produced a robust signal increase detectable in the 572 nm channel while a minor signal was observed at 615 nm. This weak signal, corresponding approximately to 6% of that measured at 572 nm, is thought to be caused by a non-specific interaction prevailing between biotinylated rabbit IgG's and Anti-rat IgG coated type 2 acceptor beads. When mixed together, increasing biotinylated rabbit and rat IgG's generated dose-dependant signal increases in 572 and 615 nm channels respectively with no apparent signal bleeding in reciprocal channels. Assay sensitivities were not significantly affected when biotinylated antibodies were used alone or in combination.

Example 3

A one well multiplexed detection of enzyme/substrate interaction and substrate modification is described in this example.

The kinase substrate ERK2 is expressed with a glutathione S-transferase tag to facilitate association with donor beads. Donor beads coated with glutathione and containing phthalocyanine are associated with the ERK2-GST fusion protein via glutathione/GST binding.

The kinase MEK1 is expressed with a histidine tag (6×His) at either the C- or N-terminus. Acceptor beads conjugated with a Ni-chelate and containing thioxene and a europium chelate are associated with the his-tagged MEK1 fusion protein via Ni/histidine tag binding.

An antibody which recognizes MEK1 phosphorylated ERK2 (mouse anti-pTpY ERK1/2) is associated with acceptor beads containing thioxene, 9,10-bis(phenylethynyl)anthracene and rubrene via anti-mouse IgG antibody binding. The antibody used, p-Tyr-100, is a generic highly promiscuous anti-phosphotyrosine antibody which recognizes both mono (pY) and dual-(pTpY) phosphorylated forms of ERK2. Better signals detected with the mono pY form of ERK2 which also appears at lower ATP concentration, thereby indicating that phosphorylation of the Tyr residue occurs before the phosphorylation of the Thr residue of the ERK2 protein.

The described donor beads and two types of acceptor beads are combined in an assay mixture. Increasing concentrations of ATP were used to promote the phosphorylation of ERK2 by MEK1. Following incubation, the mixture was irradiated at 680 nm and emission at 615 nm (indicative of interaction between MEK1 and ERK2) and 575 nm (indicative of phosphorylation of ERK2 by MEK1) was detected.

Figure 3:
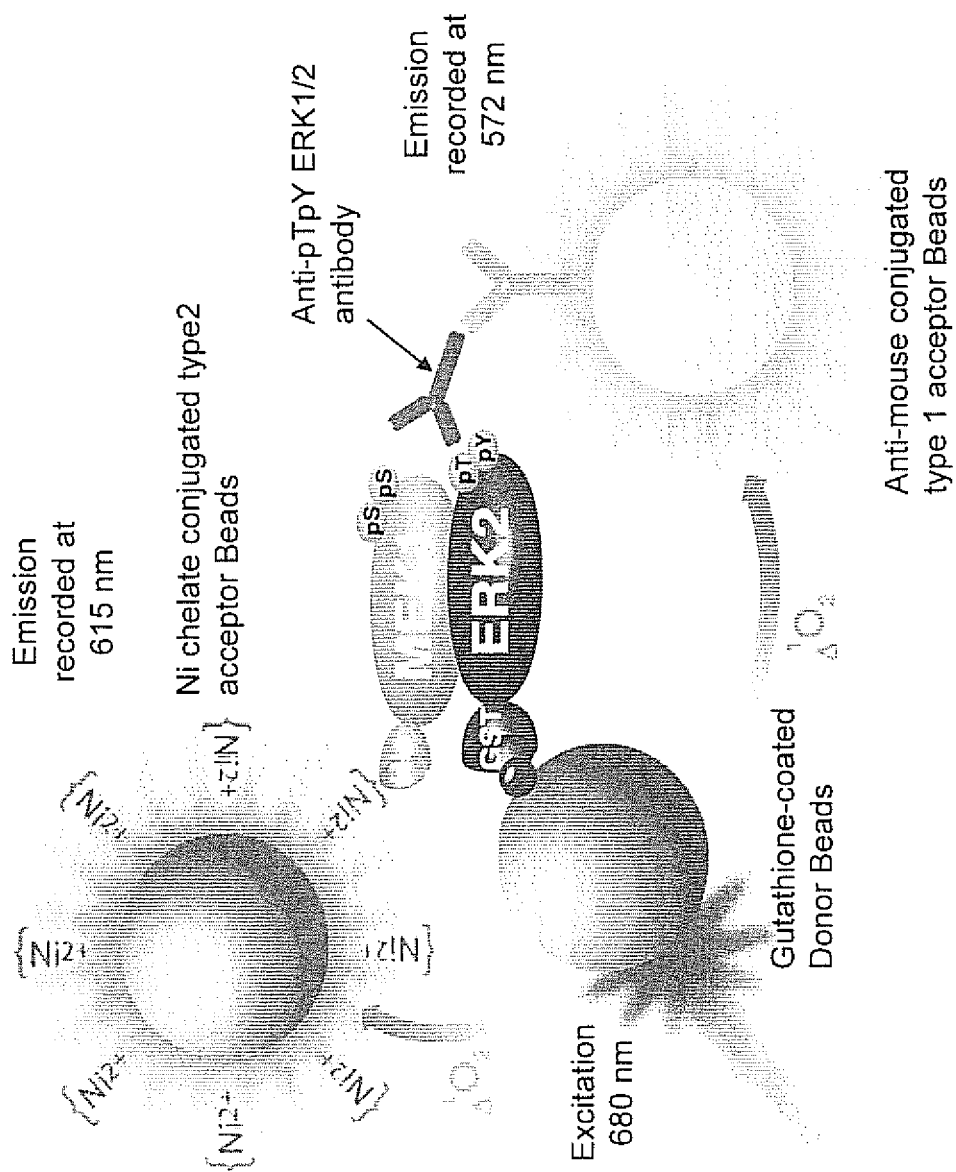
FIG. 3 is an image schematically showing an assay method and composition according to embodiments of the present invention for enzyme/enzyme substrate interaction and biological activity.

FIG. 3 schematically shows the donor and acceptor beads and the assayed interactions and activities.

Figure 4:
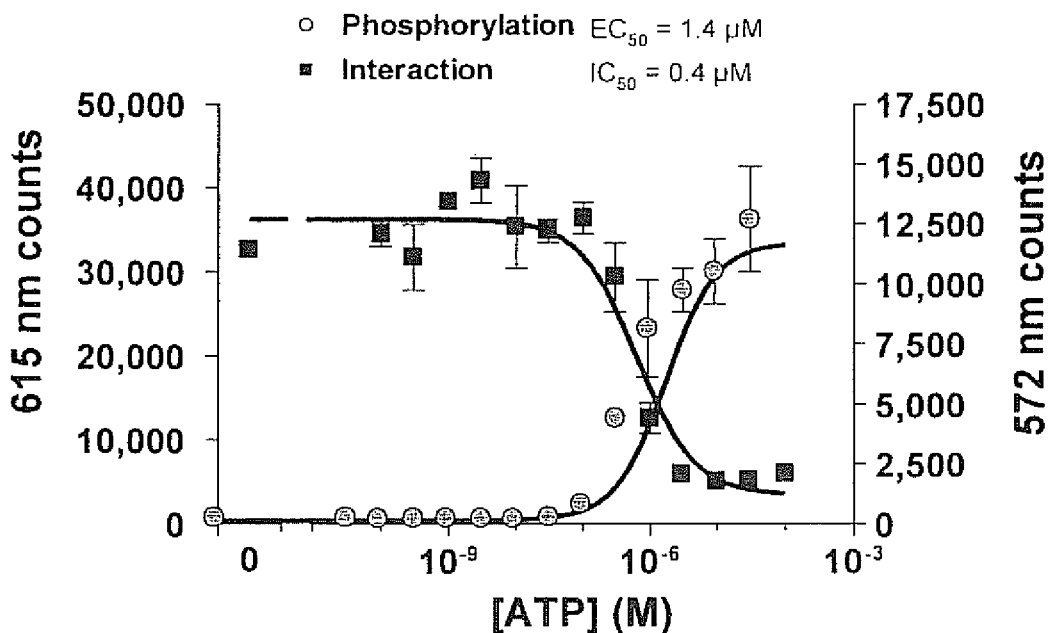
FIG. 4 is a graph showing results of an assay method and composition according to embodiments of the present invention for enzyme/enzyme substrate interaction and biological activity.

FIG. 4 shows results of this assay. In the graph shown, a first signal detected at 615 nm decreases in proportion to increasing ATP concentrations. This is explained by the decreased affinity of phosphorylated ERK2 for MEK1 compared to non-phosphoylated ERK2. A second signal detected at 572 nm increases in proportion to the concentration of ATP used to induce ERK2 phosphorylation by MEK1. $EC_{50}$ values for ATP-induced ERK2 phosphorylation and MEK1/ERK2 dissociation coincide around 1 µM ATP.

Example 4

A one well multiplexed detection of multiple substrate modifications is described in this example.

The kinase substrate ERK2 is expressed with a glutathione S-transferase tag to facilitate association with donor beads. Donor beads coated with glutathione and containing phthalocyanine are associated with the ERK2-GST fusion protein via glutathione/GST binding.

An antibody specific for a first MEK1 phosphorylated ERK2 site (P-TYR-100) is associated with acceptor beads containing thioxene, 9,10-bis(phenylethynyl)anthracene and rubrene.

An antibody specific for a second MEK1 phosphorylated ERK2 site (mouse anti-pTpY ERK1/2) is associated with acceptor beads containing thioxene and a europium chelate via anti-mouse IgG antibody binding.

The described donor beads and two types of acceptor beads are combined in an assay mixture. Increasing concentrations of ATP were used to promote the phosphorylation of ERK2 by MEK1. Following incubation, the mixture was irradiated at 680 nm and emission at 615 nm (indicative of ERK2 phosphorylation by MEK1 at a first phosphorylation site-Tyr 185) and 575 nm (indicative of phosphorylation of ERK2 by MEK1 at a second phosphorylation site-Thr 183) was detected.

Figure 5:
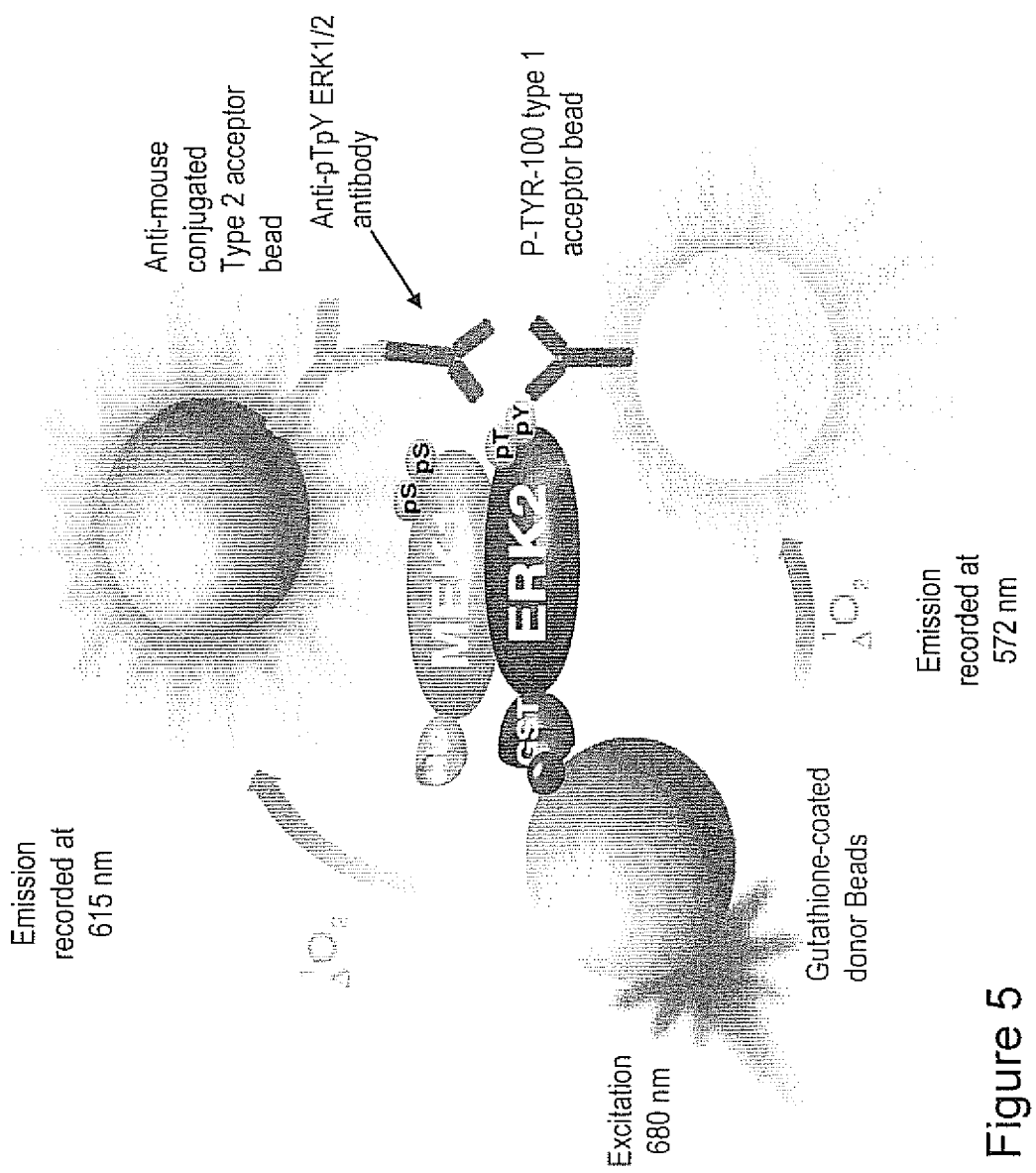
FIG. 5 is an image schematically showing an assay method and composition according to embodiments of the present invention indicative of ordered phosphorylation of a kinase substrate.

FIG. 5 schematically shows the donor and acceptor beads and the assayed interactions and activities.

Figure 6:
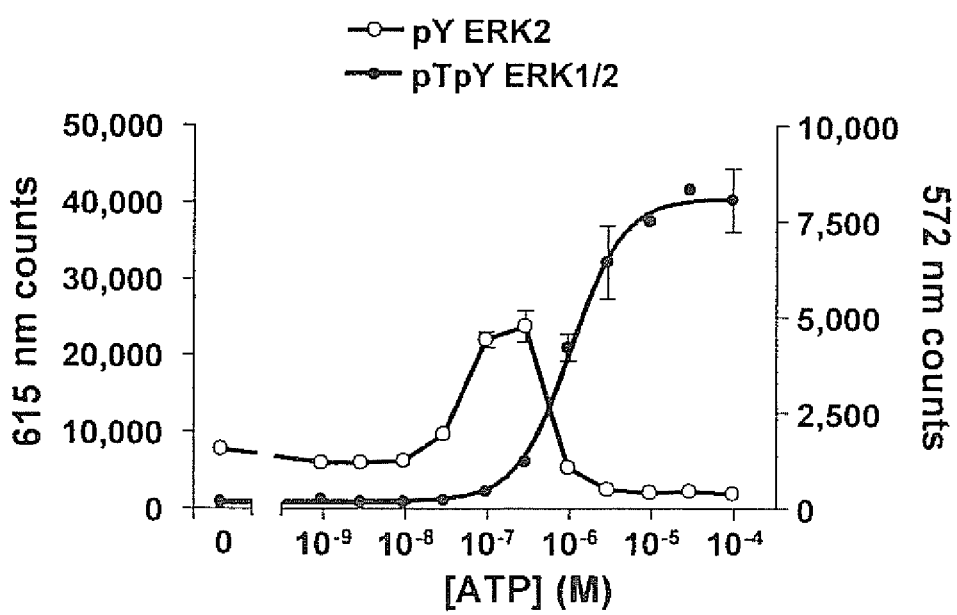
FIG. 6 is a graph showing results of an assay method and composition according to embodiments of the present invention for ordered phosphorylation of a kinase substrate.
Figure 7:
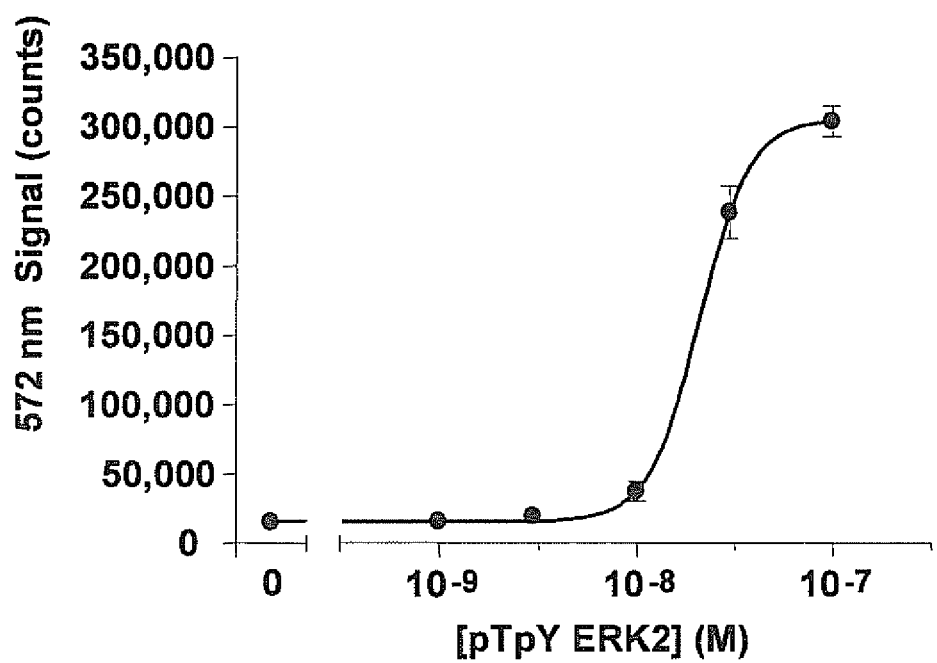
FIG. 7 is a graph showing results of an assay method and composition according to embodiments of the present invention for ordered phosphorylation of a kinase substrate.
Figures 8A, 8B:
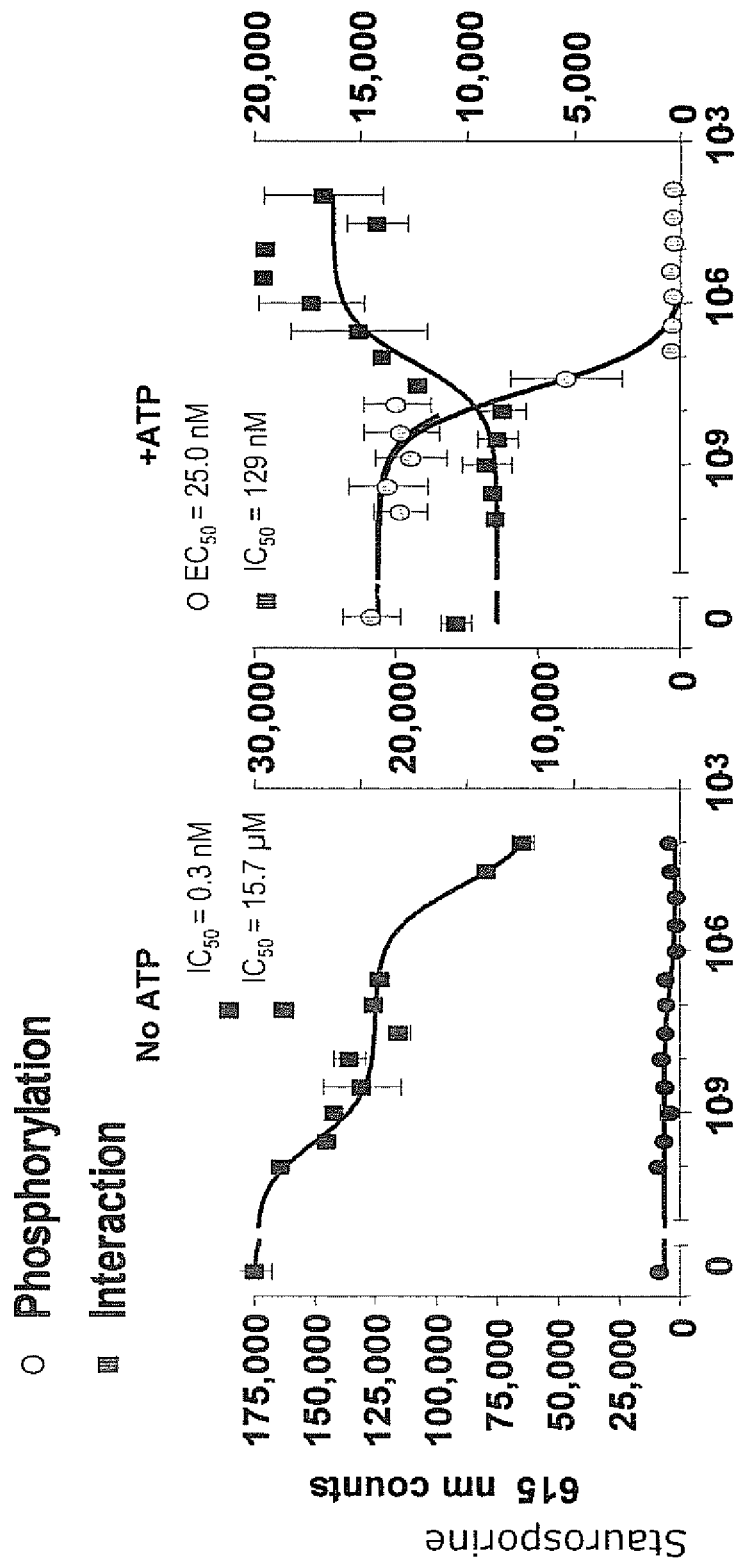
FIGS. 8A-8F show a set of graphs showing results of an assay method and composition according to embodiments of the present invention for enzyme/enzyme substrate interaction and biological activity and use to determine inhibitory activity of one or more test compounds.
Figures 8C, 8D:
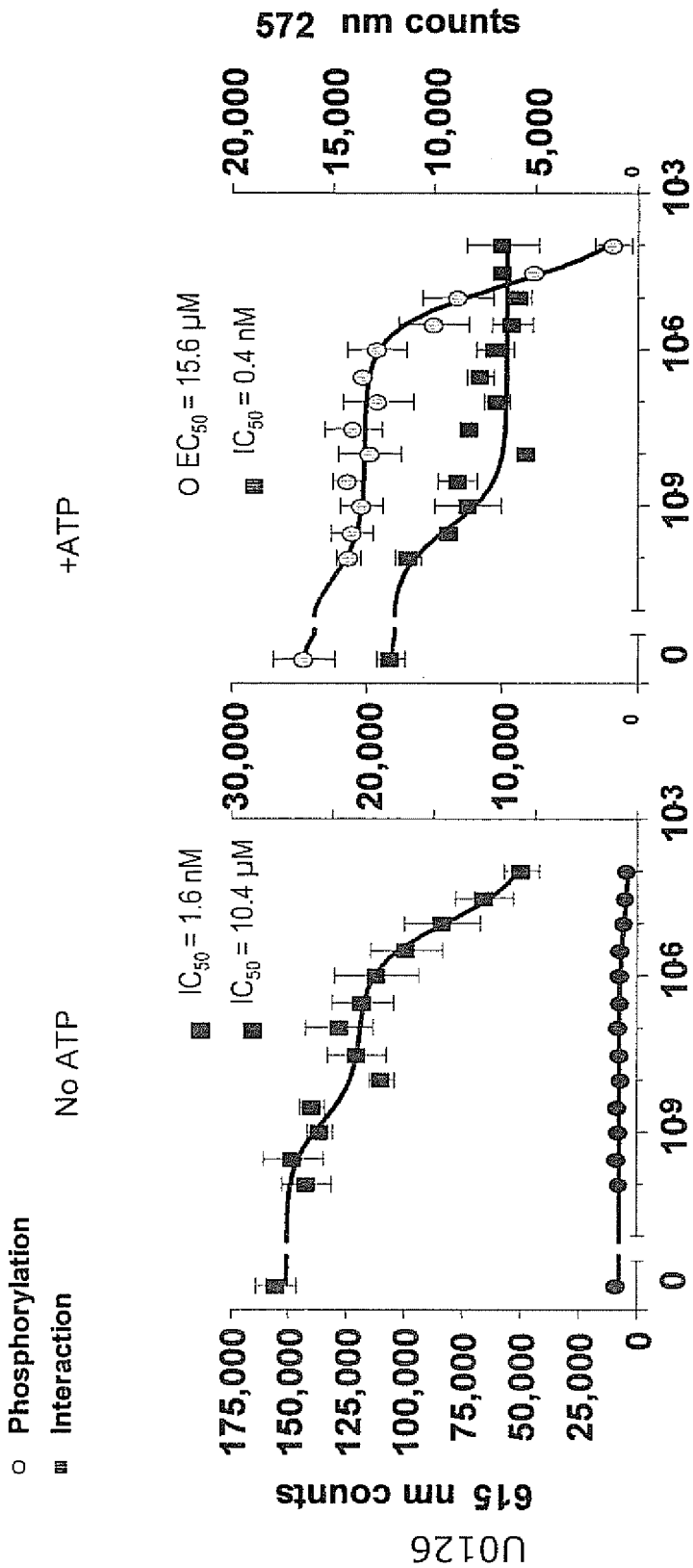
Figures 8E, 8F:
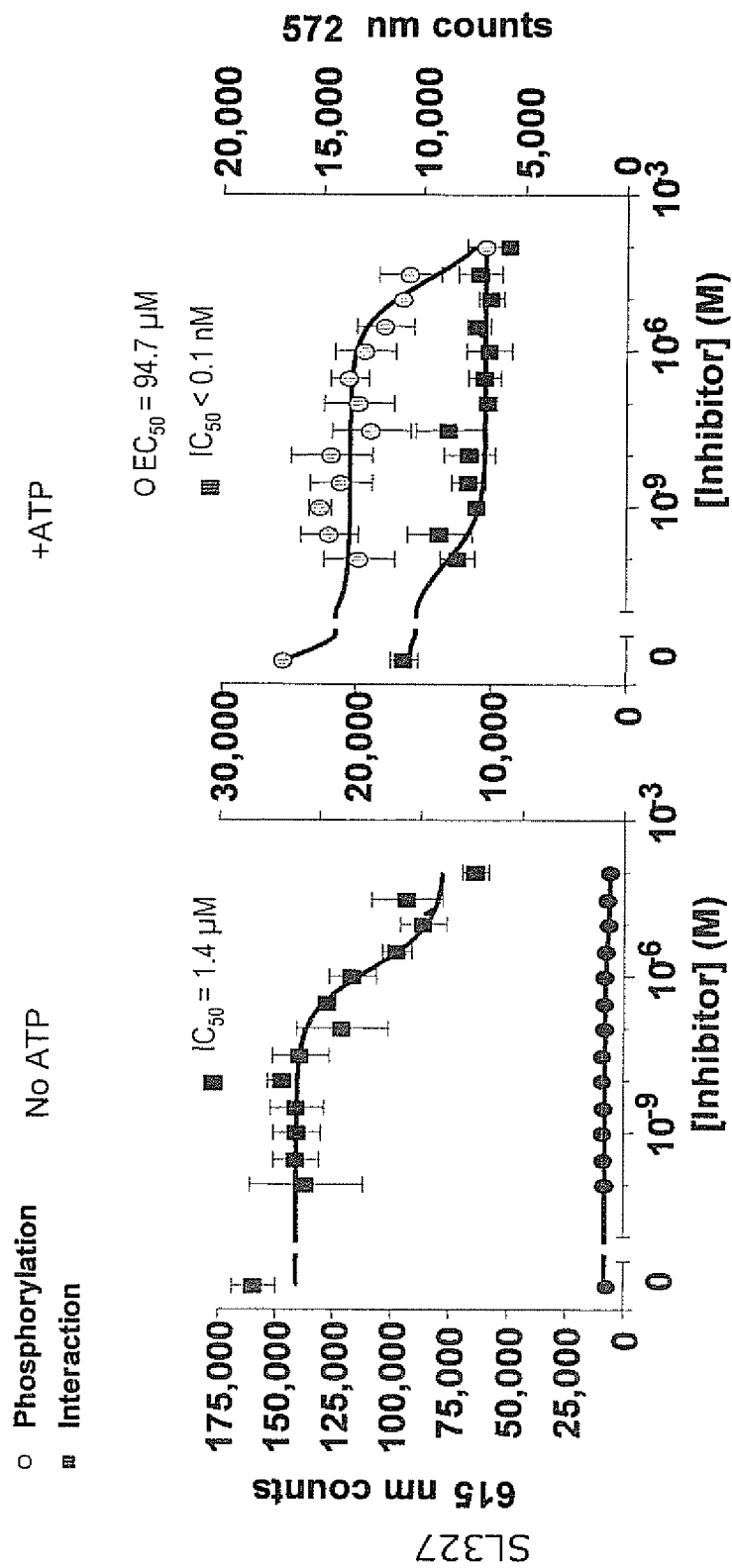

FIGS. 6 and 7 show results of this assay. The result shown in FIG. 7 indicates that the loss pf pTyr signal observed in FIG. 6 is not due to antibody "hooking" effect, further confirming phosphorylation order.

Example 5

A one well multiplexed detection of enzyme/substrate interaction and substrate modification is described in this example used to detect effects of putative enzyme inhibitors.

The kinase substrate ERK2 or a non-active variant thereof is expressed with a glutathione S-transferase tag to facilitate association with donor beads. Donor beads coated with glutathione and containing phthalocyanine are associated with the ERK2-GST fusion protein via glutathione/GST binding.

The kinase MEK1 or a non-active variant thereof is expressed with a histidine tag (6×His) at either the C- or N-terminus. Acceptor beads conjugated with a Ni-chelate and containing thioxene and a europium chelate are associated with the his-tagged MEK1 fusion protein via Ni/histidine tag binding.

An antibody specific for MEK1 phosphorylated ERK2 (mouse anti-pTpY ERK1/2) is associated with acceptor beads containing thioxene, anthracene and rubrene via anti-mouse IgG antibody binding.

The described donor beads and two types of acceptor beads are combined in an assay mixture. Increasing concentrations of putative kinase inhibitors were included in the presence or absence of 10 µm ATP to determine the effects on kinase/substrate interaction and/or kinase activity. Following incubation, the mixture was irradiated at 680 nm and emission at 615 nm (indicative of interaction between MEK1 and ERK2) and 575 nm (indicative of phosphorylation of ERK2 by MEK1) was detected.

FIGS. 8A-8F show results of this assay. All three tested inhibitors, staurosporine, U0126 and SL327 affect binding of unactive MEK1 and ERK2. The mechanism of inhibition of active MEK1 differs between the inhibitors. The poorly selective ATP competitor staurosporine perturbs ERK2 phosphorylation while partially rescuing its interaction with MEK1. U0126, a reported Raf and MEK1/2 inhibitor displays allosteric effects on MEK1. The MEK1/2 inhibitor SL327 is a U0126 derivative which behaves similarly to the parent inhibitor. Thus, the assay has utility to discriminate the mechanism of action of a test compound. The assay described in this example allows a user to discriminate between a catalytic site ATP competitor and an allosteric modulator.

Example 6

A one well multiplexed detection of enzyme/substrate interaction and substrate modification is described in this example used to detect assay specificity.

The kinase substrate ERK2 or a non-active variant thereof is expressed with a glutathione S-transferase tag to facilitate association with donor beads. Donor beads coated with glutathione and containing phthalocyanine are associated with the ERK2-GST fusion protein via glutathione/GST binding.

The kinase MEK1 or a non-active variant thereof is expressed with a histidine tag (6xHis) at either the C- or N-terminus. Acceptor beads conjugated with a Ni-chelate and containing thioxene and a europium chelate are associated with the his-tagged MEK1 fusion protein via Ni/histidine tag binding.

An antibody specific for MEK1 phosphorylated ERK2 (mouse anti-pTpY ERK1/2) is associated with acceptor beads containing thioxene, 9,10-bis(phenylethynyl)anthracene and rubrene via anti-mouse IgG antibody binding.

Figure 9:
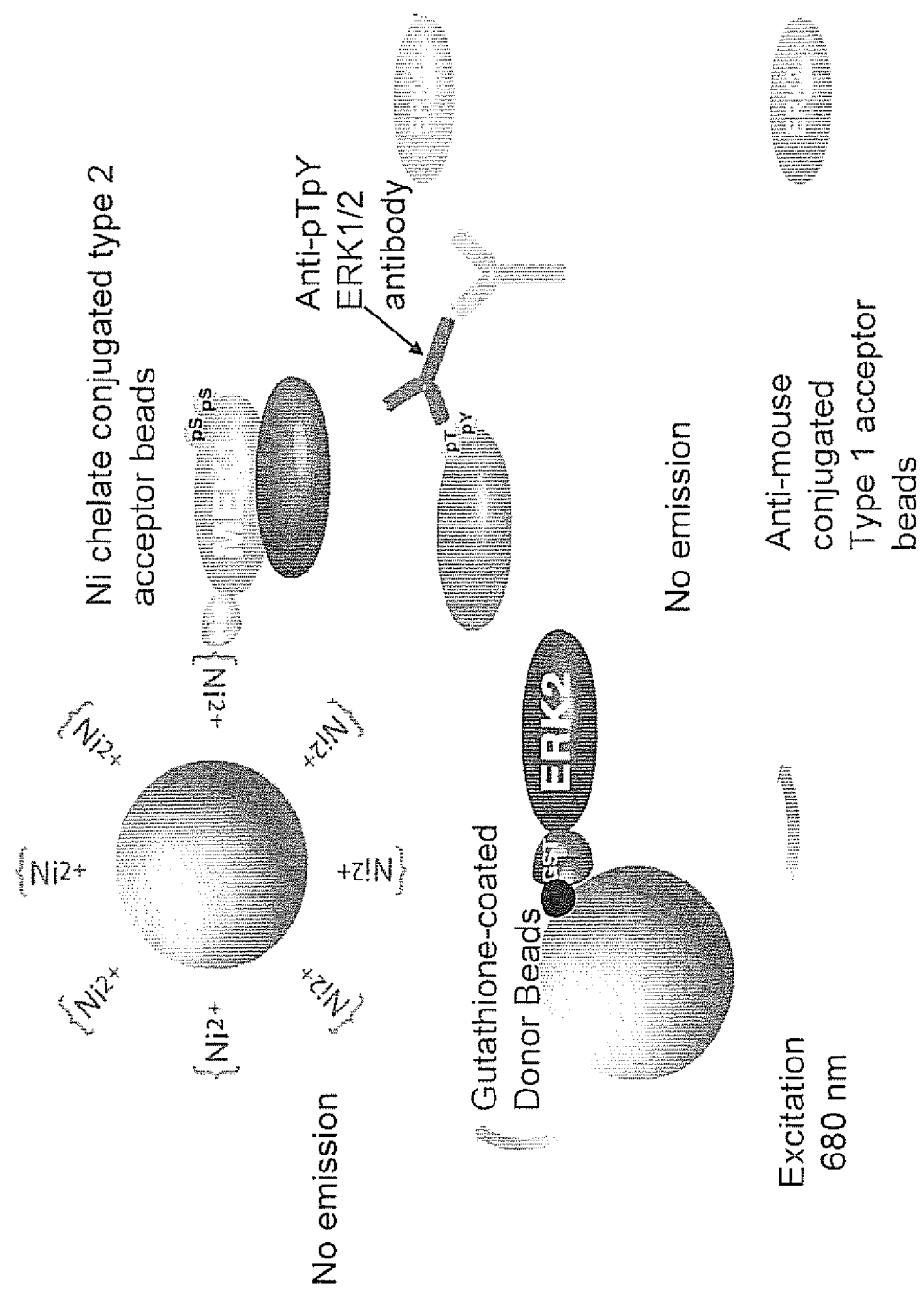
FIG. 9 is an image schematically showing an assay method and composition according to embodiments of the present invention indicative of specificity of the assay.
Figures 10A, 10B:
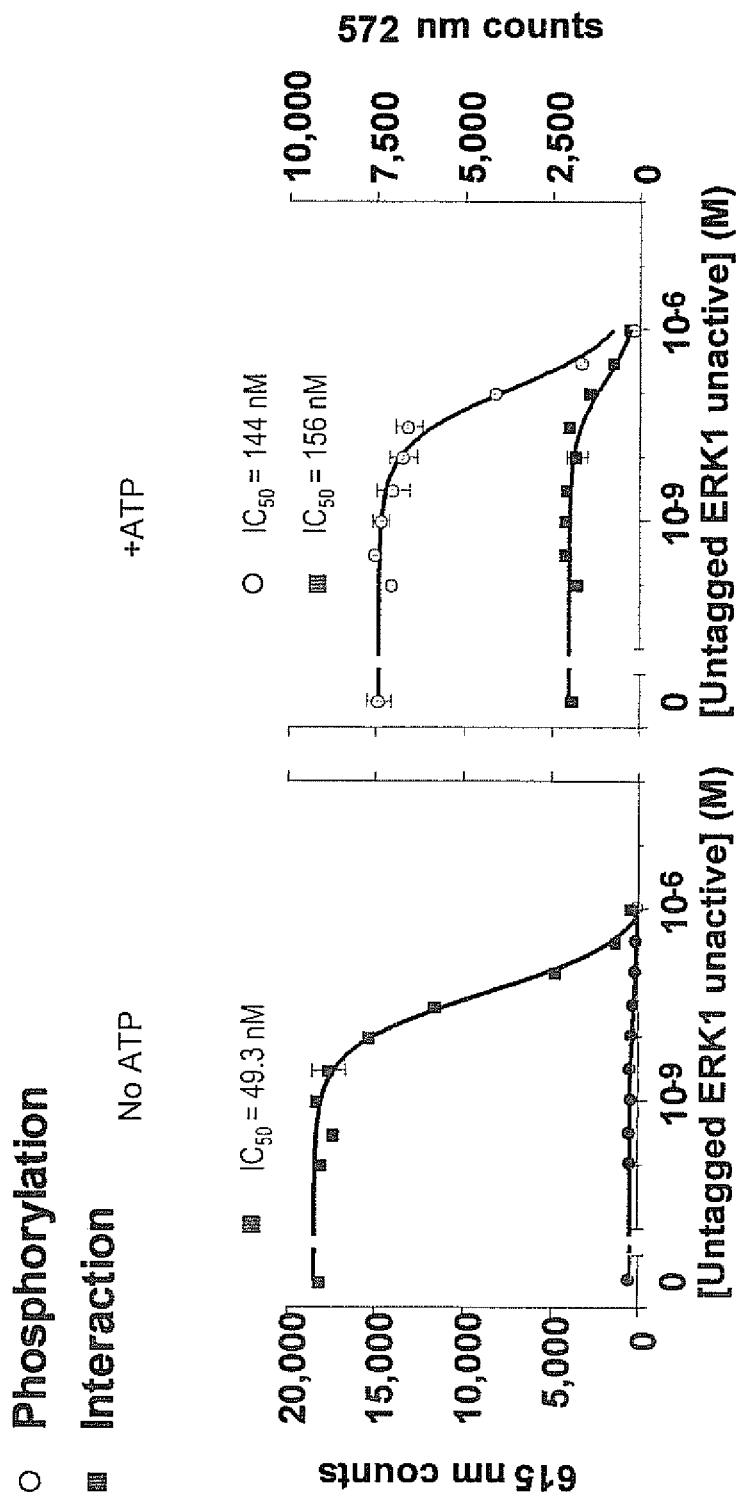
FIGS. 10A-10F show a set of graphs showing results of an assay method and composition according to embodiments of the present invention indicative of specificity of the assay.
Figures 10C, 10D:
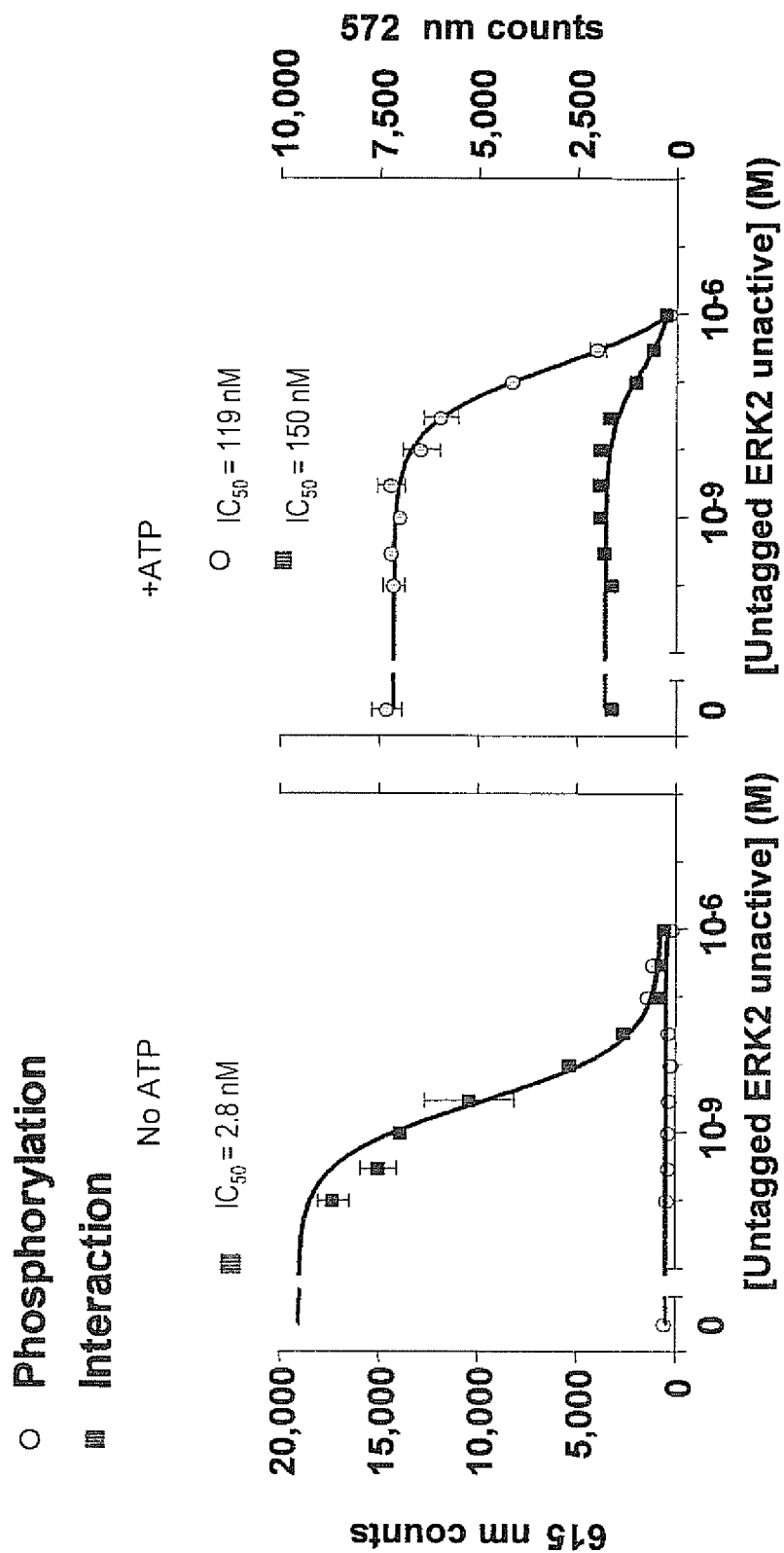
Figures 10E, 10F:
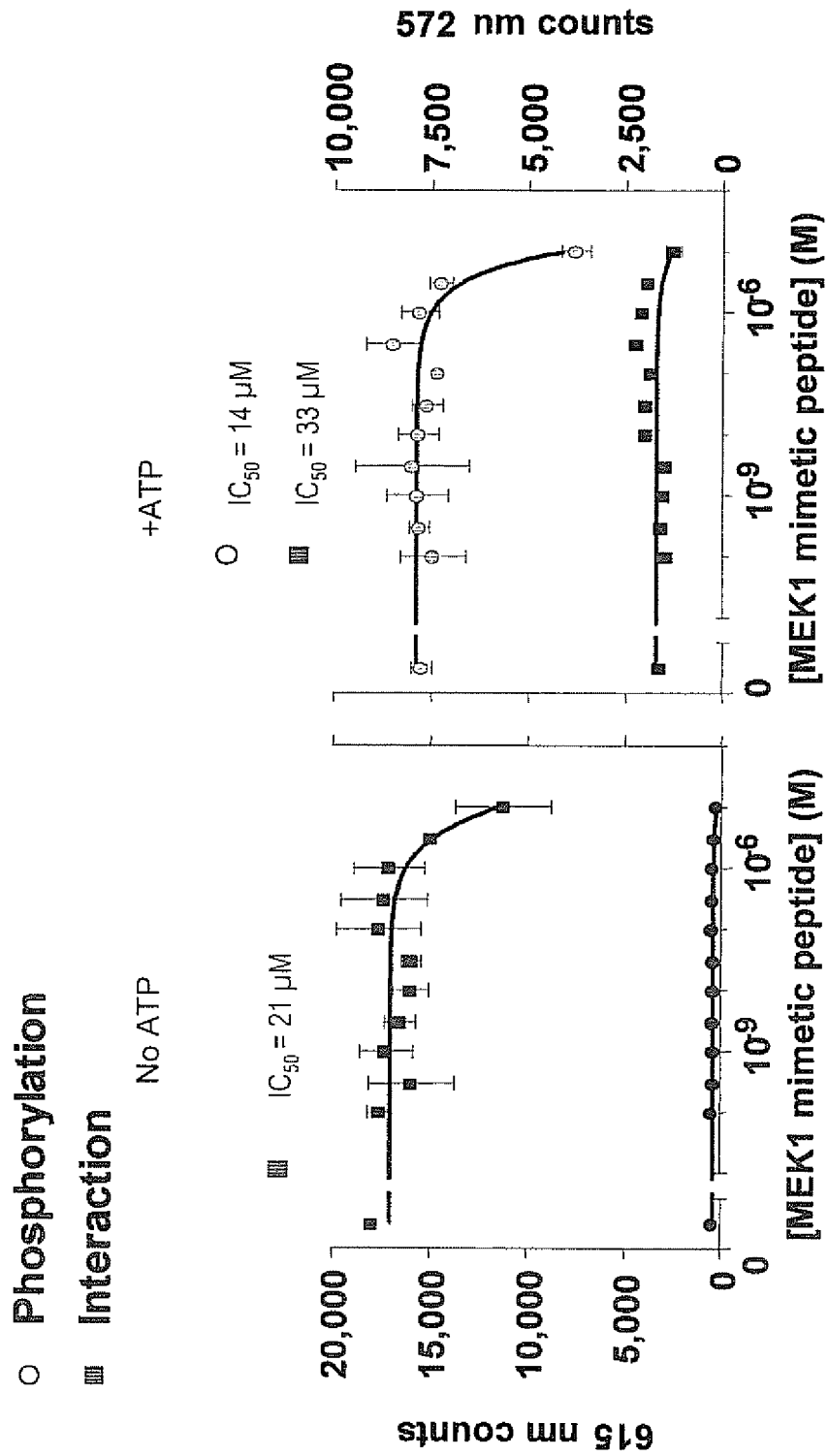
Figure 11A:
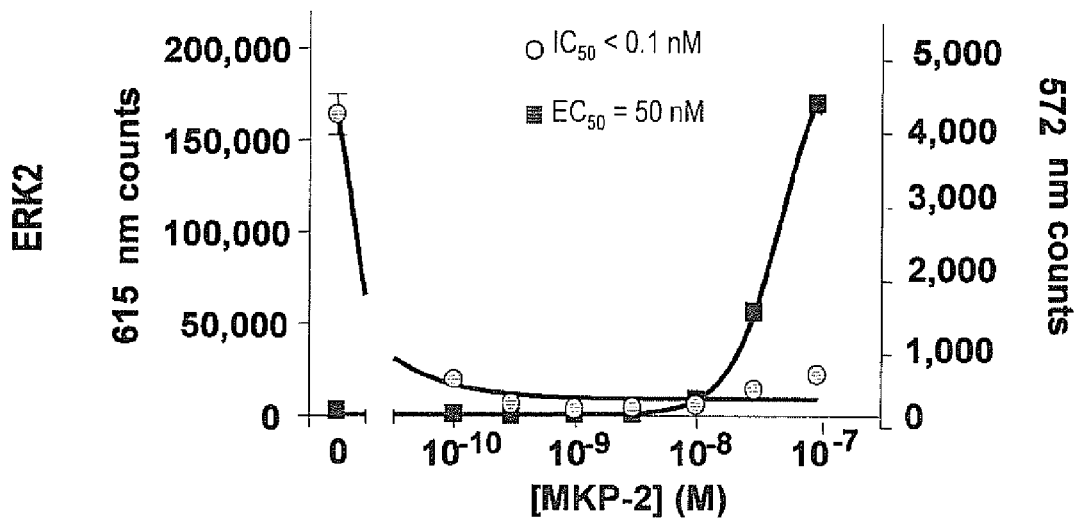
FIGS. 11A-11F show a set of graphs showing results of an assay method and composition according to embodiments of the present invention enzyme/enzyme substrate interaction and biological activity and use to determine dephosphorylation activity of one or more test compounds.
Figure 11B:
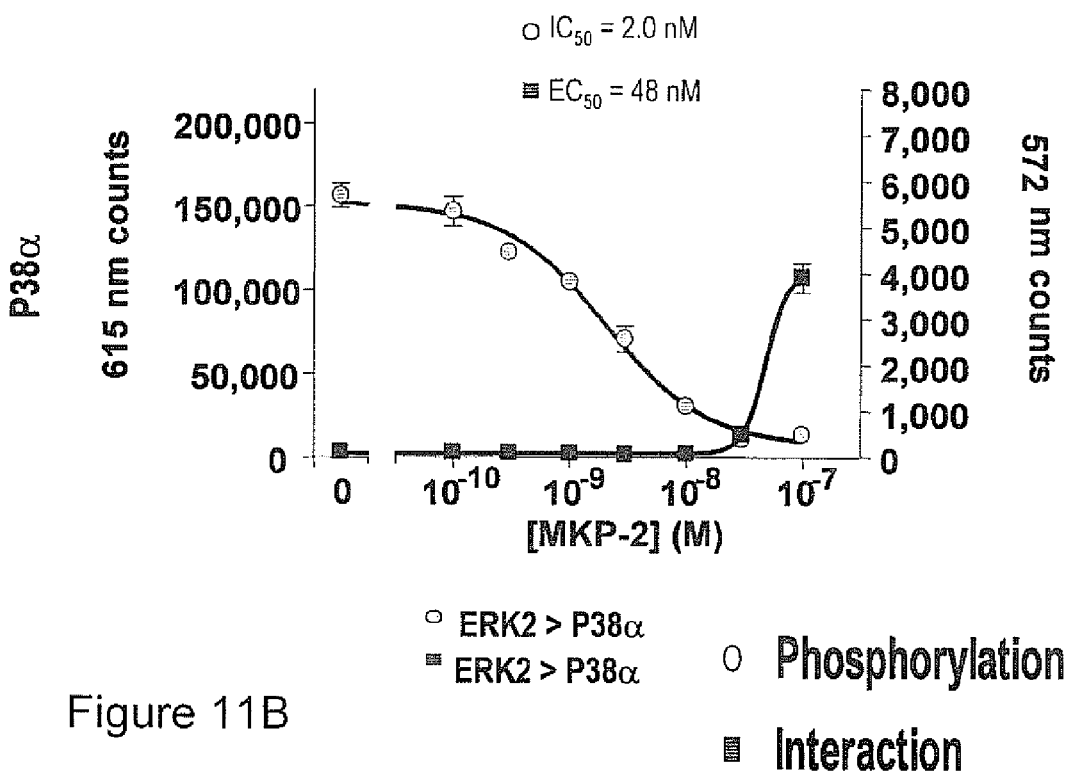
Figure 11C:
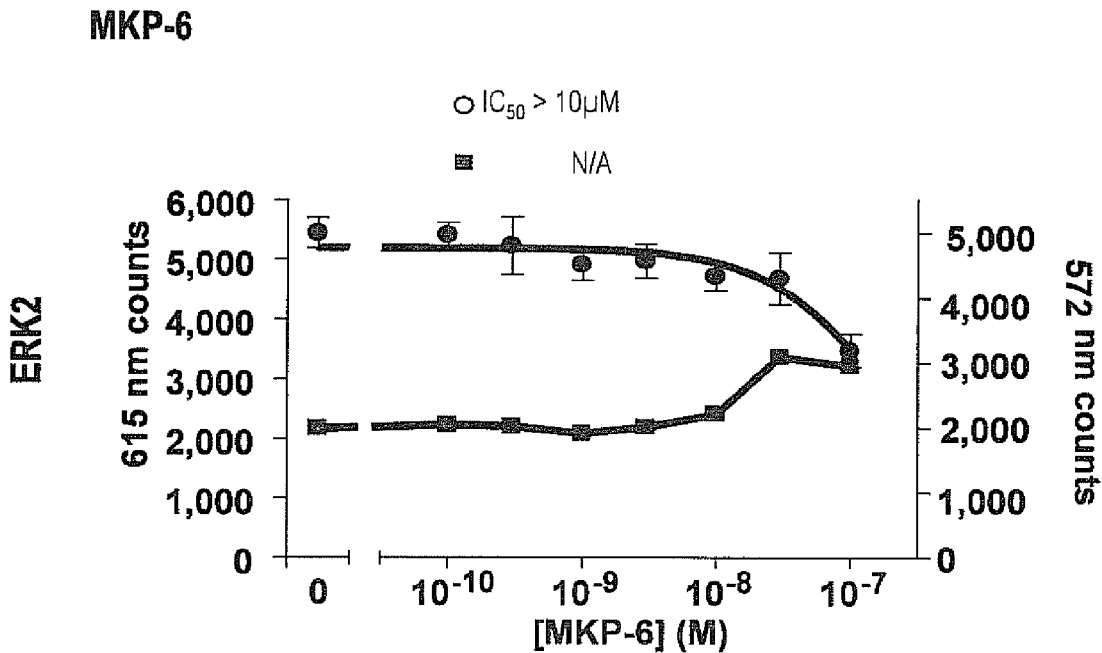
Figure 11D:
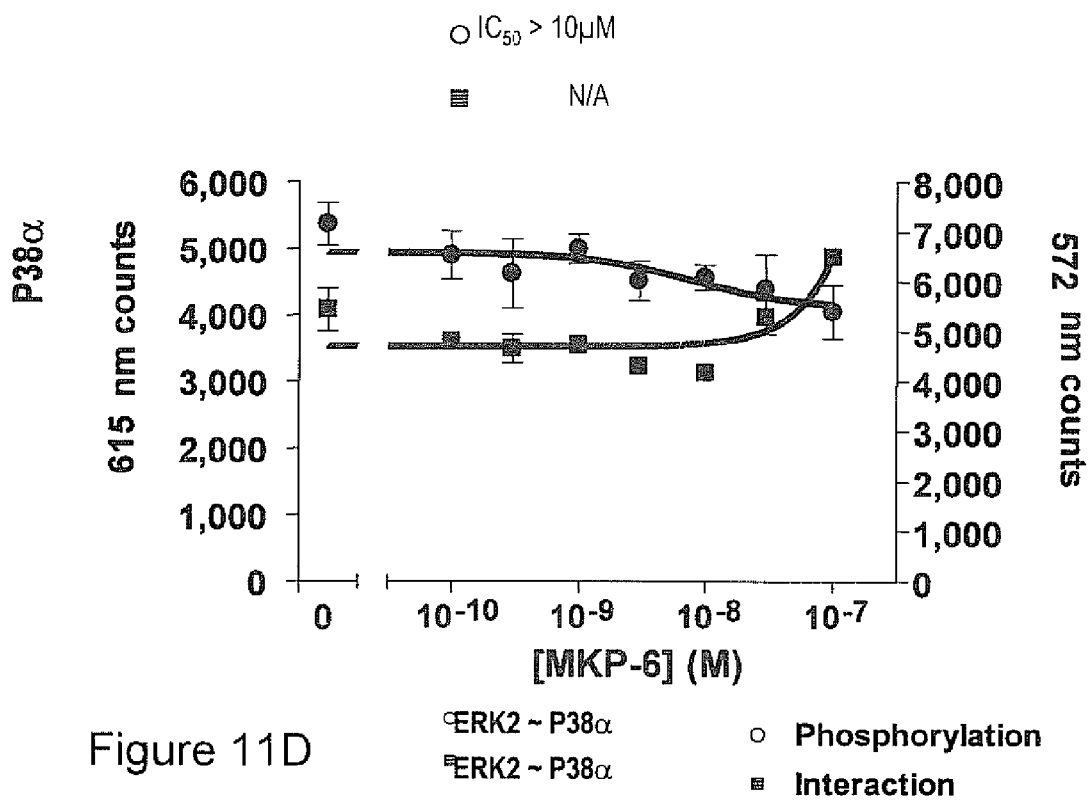
Figure 11E:
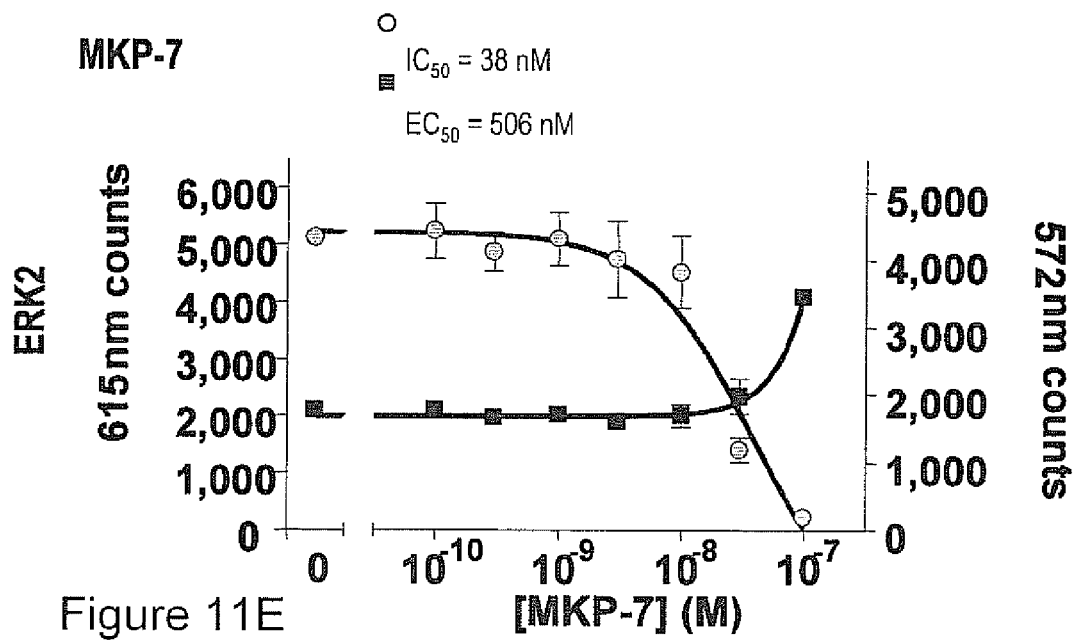
Figure 11F:
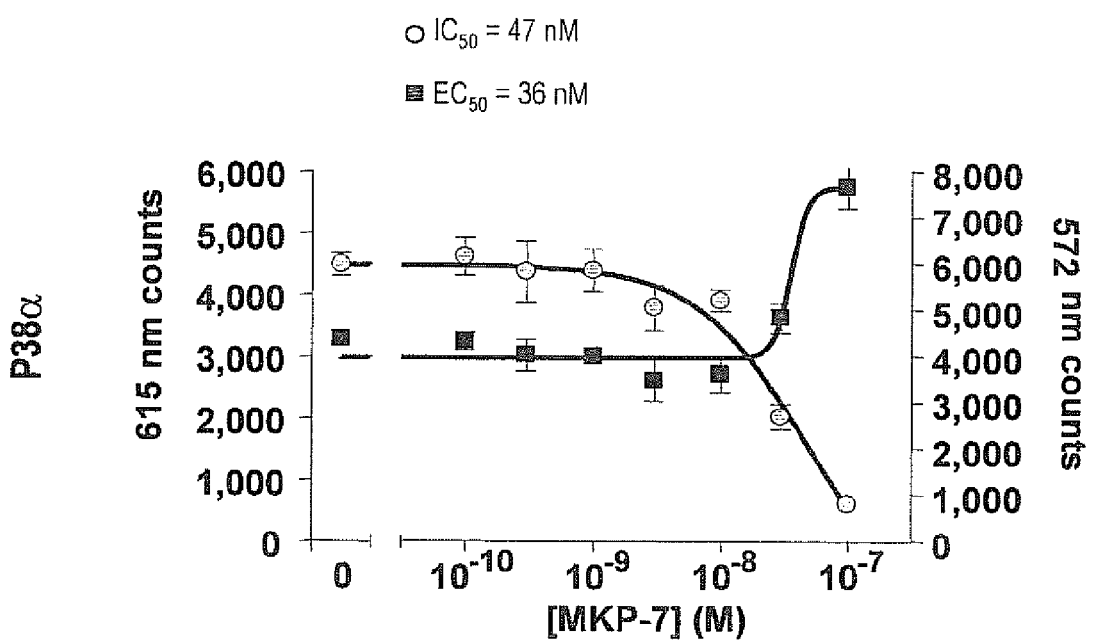

FIG. 9 schematically shows the donor and acceptor beads and the assayed interactions and activities.

The described donor beads and two types of acceptor beads are combined in an assay mixture in the presence or absence of 10 μm ATP and with various amounts of unactive ERK2 or a peptide mimicking the ERK-binding region in MEK1 to determine assay specificity. The unactive ERK2 and peptide are not associated with a bead, donor or acceptor substance.

Following incubation, the mixture was irradiated at 680 nm and emission at 615 nm (indicative of interaction between MEK1 and ERK2) and 575 nm (indicative of phosphorylation of ERK2 by MEK1) was detected.

FIGS. 10A-10F show results of this assay.

Example 7

A one well multiplexed detection of enzyme/substrate interaction and substrate modification is described in this example used to detect effects of putative modifying enzymes The kinase substrates ERK2 and p38alpha are expressed with a glutathione S-transferase tag to facilitate association with donor beads. Donor beads coated with glutathione and containing phthalocyanine are associated with the p38alpha-GST fusion protein or ERK2-GST fusion protein via glutathione/GST binding.

Three different MKP phosphatases, MKP-2, MKP-6 and MKP-7 are expressed with a histidine tag (6xHis) at either the C- or N-terminus. Acceptor beads conjugated with a Ni-chelate and containing thioxene and a europium chelate are associated with the his-tagged MEK1 fusion protein via Ni/histidine tag binding.

An antibody specific for MEK1 phosphorylated ERK2 (mouse anti-pTpY ERK1/2) is associated with acceptor beads containing thioxene, 9,10-bis(phenylethynyl)anthracene and rubrene via anti-mouse IgG antibody binding.

The described donor beads and two types of acceptor beads are combined in several assay mixtures with different phosphatase/kinase substrate combinations. Following incubation, the mixture was irradiated at 680 nm and emission at 615 nm (indicative of interaction between an MKP and ERK2) and 572 nm (indicative of phosphorylation/dephosphorylation at an ERK 2 phosphorylation site) was detected.

FIGS. 11A-11F show results of this assay.

Example 8

CHO hM2 cells (Chinese Hamster Ovary cell line stably transfected with the human M2 muscarinic receptor) were loaded with phthalocyanine and then probed with either wheat germ agglutinin (WGA, a lectin with an affinity for sialic acid/N-acetylglucosamine moieties on proteins)-conjugated acceptor beads or with bovine serum albumin (BSA)-conjugated acceptor beads, as negative control.

About 20,000 to 40,000 CHO hM2 cells of are incubated at room temperature or at 4° C. with 10 μM to 30 μM $Al^{3+}$-, $Cu^{2+}$-, or $Zn^{2+}$-phthalocyanine in cell culture medium. The phthalocyanine-loaded cells are washed several times in buffer following the incubation to remove excess phthalocyanine. About 20 to 40 μg/ml of the WGA-conjugated acceptor beads including a thioxene and europium chelate emission system are added to the assay mix with the phthalocyanine-loaded cells and incubated for 1 hour at room temperature. The assay mixtures were exposed to 680 nm light, a resulting light signal emitted from the assay mixture in the range of 520-620 nm was read on an ENVISION fluorescence reader (PerkinElmer) and good signal to background was obtained.

Example 9

Bombesin receptor is a well-characterized cell surface receptor which is known to internalize and decrease in cell surface expression following agonist (bombesin) binding. Balb3T3 cells expressing human bombesin (hBombesin) 3 with a FLAG tag and Balb3T3 cells expressing human bombesin 3 without a FLAG tag were used to monitor the expression and binding activity of the bombesin receptor, GPCR in these cells.

About 20,000 to 40,000 Balb3T3 cells expressing hBombesin-FLAG tag or untagged hBombesin are incubated at 4° C. with 10 μM to 30 μM $Al^{3+}$-phthalocyanine in cell culture medium. The phthalocyanine-loaded cells are washed several times in IVIES or HEPES buffer following the incubation to remove excess phthalocyanine. About 20 to 40 μg/ml of the anti-FLAG antibody-conjugated acceptor beads including a thioxene and europium chelate emission system are added to the assay mix including IVIES or HEPES buffer and the phthalocyanine-loaded cells and incubated for 1 hour at room temperature. The assay mixtures were exposed to 680 nm light, a resulting light signal emitted from the assay mixture in the range of 520-620 nm was read on an ENVISION fluorescence reader (PerkinElmer) and good signal to background was obtained. The FLAG-tagged hBombesin was detected with anti-FLAG Acceptor beads in the assay.

Example 10

Balb3T3 cells expressing human bombesin (hBombesin) 3 with a FLAG tag and Balb3T3 cells expressing human bombesin 3 without a FLAG tag were used to monitor the expression and binding activity of the bombesin receptor, GPCR in these cells.

About 20,000 to 40,000 Balb3T3 cells expressing hBombesin-FLAG tag or untagged hBombesin are incubated at 4° C. with 10 μM to 30 μM $Al^{3+}$-phthalocyanine in cell culture medium. The phthalocyanine-loaded cells are washed several times in MES or HEPES buffer following the incubation to remove excess phthalocyanine. About 20 to 40 μg/ml of the anti-FLAG antibody-conjugated acceptor beads including a thioxene and europium chelate emission system are added to the assay mix including MES or HEPES buffer and the phthalocyanine-loaded cells and incubated for 1 hour at room temperature. The assay mixtures were exposed to 680 nm light, a resulting light signal emitted from the assay mixture in the range of 520-620 nm was read on an ENVISION fluorescence reader (PerkinElmer) and good signal to background was obtained. The FLAG-tagged hBombesin was detected with anti-FLAG Acceptor beads in the assay.

Example 11

About 10 nM or 300 nM of the Bombesin peptide agonist, (6-14)[D-tyr6, b-Ala11, Phe13, Nle14] was incubated with Balb3T3 hBombesin 3 FLAG cells and Balb3T3 hBombesin WT cells for 1 hour at 37° C. after which cells were harvested, labeled with 10 μM to 30 μM Al$^{3+}$-phthalocyanine. The phthalocyanine-loaded cells are washed several times in MES or HEPES buffer following the incubation to remove excess phthalocyanine. About 20 to 40 of the anti-FLAG antibody-conjugated acceptor beads including a thioxene and europium chelate emission system are added to the assay mix including MES or HEPES buffer and the phthalocyanine-loaded cells and incubated for 1 hour at room temperature. The assay mixtures were exposed to 680 nm light, a resulting light signal emitted from the assay mixture in the range of 520-620 nm was read on an ENVISION fluorescence reader (PerkinElmer) and good signal to background was obtained. The FLAG-tagged hBombesin was detected with anti-FLAG Acceptor beads in the assay. Changes in surface expression of the bombesin receptor following agonist stimulation are detected.

Example 12

A one well multiplexed detection of enzyme/substrate interaction and substrate modification is described in this example used to detect a cascade of enzyme reactions.

The kinase MEK1 is expressed for introduction into an assay mixture. The enzyme is phosphorylated (active) prior to inclusion in the mixture.

The kinase substrate ERK2 is expressed with a glutathione S-transferase tag to facilitate association with donor beads. Donor beads coated with glutathione and containing phthalocyanine are associated with the ERK2-GST fusion protein via glutathione/GST binding.

The kinase substrate Elk-1 is expressed with a glutathione S-transferase tag to facilitate association with donor beads. Donor beads coated with glutathione and containing phthalocyanine are associated with the Elk-1-GST fusion protein via glutathione/GST binding.

An antibody that recognizes MEK1 phosphorylated ERK2 (mouse anti-pTpY ERK1/2) is associated with acceptor beads containing thioxene, 9,10-bis(phenylethynyl)anthracene and rubrene via anti-mouse IgG antibody binding.

An antibody that recognizes ERK2 phosphorylated Elk-1 (anti-pS383 Elk-1) is associated with acceptor beads containing thioxene and a europium chelate via protein A binding.

The described donor beads and two types of acceptor beads are combined in an assay mixture.

Following incubation, the mixture was irradiated at 680 nm and emission at 615 nm (indicative of phosphorylation of Elk-1 by ERK2) and 555 nm (indicative of phosphorylation of ERK2 by MEK1) was detected. The assay allows for screening of test compounds to determine their target in an enzyme cascade.

Example 13

A one well multiplexed detection of enzyme/substrate interaction and substrate modification is described in this example used to detect multiple interactions of specific binding agents.

The kinase MEK1 is expressed with a histidine tag (6×His) at either the C- or N-terminus. Acceptor beads conjugated with a Ni-chelate and containing thioxene and a europium chelate are associated with the his-tagged MEK1 fusion protein via Ni/histidine tag binding.

The kinase substrate ERK2 is expressed with a glutathione S-transferase tag to facilitate association with donor beads. Donor beads coated with glutathione and containing phthalocyanine are associated with the ERK2-GST fusion protein via glutathione/GST binding.

The kinase substrate Elk-1 is expressed with a FLAG tag to facilitate association with acceptor beads containing thioxene, 9,10-bis(phenylethynyl)anthracene and rubrene via anti-FLAG antibody binding.

The described donor beads and two types of acceptor beads are combined in an assay mixture.

Following incubation, the mixture was irradiated at 680 nm and emission at 615 nm (indicative of interaction of MEK1 and ERK2) and 555 nm (indicative of interaction of ERK2 and Elk-1) was detected. The assay generally allows for detection and monitoring of association order, mutually exclusive relationships, scaffolding proteins and multimeric complexes.

Example 14

A one well multiplexed detection of enzyme/substrate interaction and substrate modification is described in this example used to determine the proportion of modified substrate in a sample.

Commercially available kinase MEK1 is introduced into an assay mixture. The enzyme is phosphorylated (active) prior to inclusion in the mixture.

The kinase substrate ERK2 is expressed with a glutathione S-transferase tag to facilitate association with donor beads. Donor beads coated with glutathione and containing phthalocyanine are associated with the ERK2-GST fusion protein via glutathione/GST binding.

An antibody that recognizes MEK1 phosphorylated ERK2 (mouse anti-pTpY ERK1/2) is associated with acceptor beads containing thioxene, 9,10-bis(phenylethynyl)anthracene and rubrene via anti-mouse IgG antibody binding.

An antibody that recognizes both MEK1-phosphorylated and non-phosphorylated ERK2 is associated with acceptor beads containing thioxene and a europium chelate.

The described donor beads and two types of acceptor beads are combined in an assay mixture.

Following incubation, the mixture was irradiated at 680 nm and emission at 615 nm (indicative of total ERK2 present in the assay mixture) and 572 nm (indicative of MEK1 phosphorylated ERK2 in the assay mixture) was detected. The assay generally allows for detection and monitoring of enzyme activity and post-translational modification of enzyme substrates.

Example 15

Multiplexed assays were performed to detect two different analytes in solution: amyloid peptides Aβ40 and Aβ42. Biotinylated amyloid peptides Aβ40 and Aβ42 are associated with streptavidin donor beads.

An antibody that recognizes amyloid peptides Aβ40 is associated with acceptor beads containing thioxene, 9,10-bis(phenylethynyl)anthracene and rubrene via anti-mouse IgG antibody binding.

An antibody that recognizes amyloid peptides Aβ42 is associated with acceptor beads containing thioxene and a europium chelate.

The described donor beads and two types of acceptor beads are combined in an assay mixture.

Following incubation, the mixture was irradiated at 680 nm and emission at 615 nm (indicative of amyloid peptide Aβ42 in the assay mixture) and 572 nm (indicative of amyloid peptides Aβ40 in the assay mixture) was detected. The assay generally allows for detection and monitoring of presence and levels of multiple analytes in a sample.

This assay has additional utility as an in-well internal interference control.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention clamed is:

1. An assay method, comprising:
   A) providing an assay mixture, comprising, in combination:
      a first interacting member, wherein the first interacting member is an enzyme,
      a second interacting member, wherein the second interacting member is a substrate for the enzyme,
      a first solid-phase support comprising a first specific binding agent selective for the first interacting member and a photosensitizer, wherein the photosensitizer is light excitable to activate oxygen to produce singlet oxygen,
      a second solid-phase support comprising a second specific binding agent selective for the second interacting member and a first emission system comprising a first energy acceptor activated by singlet oxygen, the first emission system activated by singlet oxygen to emit a first light signal characterized by a first emission spectrum, wherein specific interaction of the first interacting member and the second interacting member brings the photosensitizer and the first emission system into proximity, such that the irradiating generates the first light signal indicative of specific interaction of the first interacting member and the second interacting member, and
      a third solid-phase support comprising a third specific binding agent selective for the second interacting member, wherein the third specific binding agent selectively interacts with enzyme-modified substrate, and a second emission system comprising a second energy acceptor activated by singlet oxygen, the second emission system activated by singlet oxygen to emit a second light signal characterized by a second emission spectrum, wherein the first light signal and second light signal are distinguishable, wherein binding of the third specific binding agent with the second interacting member brings the photosensitizer and the second emission system into proximity, such that the irradiating generates the second light signal indicative of binding of the third specific binding agent and second interacting member,
   B) irradiating the assay mixture with a light source, thereby activating the photosensitizer to produce singlet oxygen; and
   C) detecting the first light signal and the second light signal, wherein detecting the first light signal is indicative of proximity of a first target bound to the first specific binding agent and a second target bound to the second specific binding agent and wherein detecting the second light signal is indicative of proximity of the first target bound to the first specific binding agent and third target bound to the third specific binding agent.

2. The assay method of claim 1, wherein the first solid-phase support, second solid-phase support and third solid-phase support are particles.

3. The assay method of claim 1, wherein the first solid-phase support, second solid-phase support and third solid-phase support are beads.

4. The assay method of claim 1, wherein the first emission spectrum is characterized by an emission maximum in the range of 545-580 nm and the second emission spectrum is characterized by an emission maximum in the range of 600-620 nm.

5. The assay method of claim 1, wherein the photosensitizer comprises phthalocyanine.

6. The assay method of claim 1, wherein the first energy acceptor and second energy acceptor activated by singlet oxygen comprise thioxene.

7. The assay method of claim 6, wherein the first emission system further comprises rubrene.

8. The assay method of claim 6, wherein the second emission system further comprises a lanthanide chelate.

9. The assay method of claim 8, wherein the lanthanide chelate is a europium chelate.

10. The assay method of claim 1, wherein the enzyme is a kinase, the substrate is a substrate of the kinase and the third specific binding agent selectively binds to the substrate phosphorylated by the kinase.

11. The assay method of claim 1, further comprising including a test compound in the assay mixture and comparing the first light signal and the second light signal in the absence of the test compound with the first light signal and the second light signal in the presence of the test compound.

12. An assay method, comprising:
    A) providing an assay mixture, comprising, in combination:
       a first interacting member, wherein the first interacting member is an enzyme substrate which is modifiable by an enzyme,
       a second interacting member, wherein the second interacting member is the enzyme,
       a first solid-phase support comprising a first specific binding agent selective for the first interacting member and a photosensitizer, wherein the photosensitizer is light excitable to activate oxygen to produce singlet oxygen,
       a second solid-phase support comprising a second specific binding agent selective for a first enzyme-modified substrate site and a first emission system comprising a first energy acceptor activated by singlet oxygen, the first emission system activated by singlet oxygen to emit a first light signal characterized by a first emission spectrum, wherein binding of the second specific binding agent with the first enzyme-modified substrate site brings the photosensitizer and the first emission system into proximity, such that the irradiating generates the first light signal indicative of specific interaction of the first interacting member and the second interacting member, and
       a third solid-phase support comprising a third specific binding agent selective for a second enzyme-modified substrate site, and a second emission system comprising a second energy acceptor activated by singlet oxygen, the second emission system activated by singlet oxygen to emit a second light signal characterized by a second emission spectrum, wherein the first light signal and second light signal are distinguishable, wherein binding of the third specific binding agent with the second enzyme-modified substrate site brings the photosensitizer and the second emission system into proximity, such that the irradiating generates the second light signal indicative of specific interaction of the first interacting member and the second interacting member, B) irradiating the assay mixture with a light source, thereby activating the photosensitizer to produce singlet oxygen; and C) detecting the first light signal and the second light signal, wherein detecting the first light signal is indicative of proximity of a first target bound to the first specific binding agent and a second target bound to the second specific binding agent and wherein detecting the second light signal is indicative of proximity of the first target bound to the first specific binding agent and third target bound to the third specific binding agent.

13. The assay method of claim 12, wherein the first solid-phase support, second solid-phase support and third solid-phase support are particles.

14. The assay method of claim 12, wherein the first solid-phase support, second solid-phase support and third solid-phase support are beads.

15. The assay method of claim 12, wherein the first emission spectrum is characterized by an emission maximum in the range of 545-580 nm and the second emission spectrum is characterized by an emission maximum in the range of 600-620 nm.

16. The assay method of claim 12, wherein the photosensitizer comprises phthalocyanine.

17. The assay method of claim 12, wherein the first energy acceptor and second energy acceptor activated by singlet oxygen comprise thioxene.

18. The assay method of claim 17, wherein the first emission system further comprises rubrene.

19. The assay method of claim 17, wherein the second emission system further comprises a lanthanide chelate.

20. The assay method of claim 19, wherein the lanthanide chelate is a europium chelate.

21. The assay method of claim 12, further comprising including a test compound in the assay mixture and comparing the first light signal and the second light signal in the absence of the test compound with the first light signal and the second light signal in the presence of the test compound.

* * * * *